(12) United States Patent
Humayun et al.

(10) Patent No.: US 10,363,165 B2
(45) Date of Patent: Jul. 30, 2019

(54) INDEPENDENT SURGICAL CENTER

(71) Applicant: Doheny Eye Institute, Los Angeles, CA (US)

(72) Inventors: Mark Humayun, Glendale, CA (US); Charles DeBoer, Los Angeles, CA (US); Ralph Kerns, Laguna Niguel, CA (US); Matthew McCormick, Yucaipa, CA (US); Prashant Bhadri, Los Angeles, CA (US); Lawrence Chong, Seal Beach, CA (US)

(73) Assignee: DOHENY EYE INSTITUTE, Los Angeles, CA (US)

( * ) Notice: Subject to any disclaimer, the term of this patent is extended or adjusted under 35 U.S.C. 154(b) by 178 days.

(21) Appl. No.: 15/656,171

(22) Filed: Jul. 21, 2017

(65) Prior Publication Data
US 2017/0319386 A1 Nov. 9, 2017

Related U.S. Application Data

(63) Continuation of application No. 14/092,159, filed on Nov. 27, 2013, now Pat. No. 9,730,833, which is a (Continued)

(51) Int. Cl.
*A61F 9/007* (2006.01)
*A61B 50/33* (2016.01)
(Continued)

(52) U.S. Cl.
CPC ...... *A61F 9/00736* (2013.01); *A61B 18/1206* (2013.01); *A61B 50/33* (2016.02); (Continued)

(58) Field of Classification Search
CPC ............ A61B 18/1206; A61B 19/0271; A61B 19/5202; A61B 2017/00199; A61B 2017/00221
See application file for complete search history.

(56) References Cited

U.S. PATENT DOCUMENTS 3,116,828 A 1/1964 Glassman
3,271,859 A 9/1966 Horowitz et al.
(Continued)

FOREIGN PATENT DOCUMENTS

CN 2289530 9/1998
EP 876799 11/1998
(Continued)

OTHER PUBLICATIONS

Extended European Search Report dated Nov. 23, 2010 for European Application No. 08746468.1, filed Apr. 21, 2008; 12 pages, Apr. 21, 2008.
(Continued)

*Primary Examiner* — Ashley L Fishback
(74) *Attorney, Agent, or Firm* — Snell & Wilmer LLP

(57) ABSTRACT

A biological tissue cutting and fluid aspiration system provides a plurality of surgical instruments operable independent of an external control console. In some embodiments, each surgical instrument may include all sensors and controls directly applicable to the surgical instrument, and may be used independently. In some embodiments, instruments communicate status information to each other, and adjust operating parameters based on the communications.

14 Claims, 10 Drawing Sheets

Related U.S. Application Data continuation of application No. 13/084,471, filed on Apr. 11, 2011, now Pat. No. 8,623,000, which is a continuation of application No. 12/107,038, filed on Apr. 21, 2008, now Pat. No. 8,177,776.

(60) Provisional application No. 60/925,546, filed on Apr. 20, 2007.

(51) Int. Cl.
| | |
|---|---|
| *A61B 17/00* | (2006.01) |
| *A61B 18/12* | (2006.01) |
| *A61B 90/30* | (2016.01) |
| *A61B 90/98* | (2016.01) |
| *A61B 50/30* | (2016.01) |
| *A61B 18/00* | (2006.01) |

(52) U.S. Cl.
CPC ............ *A61B 90/30* (2016.02); *A61B 90/98* (2016.02); *A61B 2017/0023* (2013.01); *A61B 2017/00199* (2013.01); *A61B 2017/00221* (2013.01); *A61B 2017/00225* (2013.01); *A61B 2017/00544* (2013.01); *A61B 2017/00734* (2013.01); *A61B 2018/00601* (2013.01); *A61B 2050/3008* (2016.02); *A61F 9/00745* (2013.01)

(56) References Cited

U.S. PATENT DOCUMENTS

| | | |
|---|---|---|
| 3,293,430 A | 12/1966 | Wustner |
| 3,304,609 A | 2/1967 | Horowitz et al. |
| 3,366,230 A | 1/1968 | Loran |
| 3,404,458 A | 10/1968 | Weiss et al. |
| 3,702,940 A | 11/1972 | Stewart |
| 3,820,656 A | 6/1974 | Orr |
| 3,884,238 A | 5/1975 | O'Malley et al. |
| 3,976,195 A | 8/1976 | Cohen |
| 3,986,263 A | 10/1976 | Borgelt et al. |
| 3,990,453 A | 11/1976 | Douvas et al. |
| 4,011,944 A | 3/1977 | Cooley et al. |
| 4,014,342 A | 3/1977 | Staub et al. |
| 4,019,514 A | 4/1977 | Banko |
| 4,108,182 A | 8/1978 | Hartman et al. |
| 4,112,947 A | 9/1978 | Nehring |
| 4,117,843 A | 10/1978 | Banko |
| 4,168,707 A | 9/1979 | Douvas et al. |
| 4,200,106 A | 4/1980 | Douvas et al. |
| 4,266,669 A | 5/1981 | Watson |
| 4,288,733 A | 9/1981 | Bilanceri et al. |
| 4,293,074 A | 10/1981 | Dunsky |
| 4,320,761 A | 3/1982 | Haddad |
| 4,324,243 A | 4/1982 | Helfgott et al. |
| 4,378,108 A | 3/1983 | Bailey, Jr. |
| 4,428,748 A | 1/1984 | Peyman et al. |
| 4,430,062 A | 2/1984 | Henrichsen et al. |
| 4,479,762 A | 10/1984 | Bilstad et al. |
| 4,735,610 A | 4/1988 | Akkas et al. |
| 4,798,580 A | 1/1989 | DeMeo et al. |
| 4,869,266 A | 9/1989 | Taylor et al. |
| 4,889,231 A | 12/1989 | Foote et al. |
| 4,903,710 A | 2/1990 | Jessamine et al. |
| 4,909,249 A | 3/1990 | Akkas et al. |
| 4,930,997 A | 6/1990 | Bennett |
| 4,974,728 A | 12/1990 | Colton |
| 4,986,827 A | 1/1991 | Akkas et al. |
| 5,007,535 A | 4/1991 | Meseke et al. |
| 5,013,240 A | 5/1991 | Bailey et al. |
| 5,019,035 A | 5/1991 | Missirlian et al. |
| 5,078,677 A | 1/1992 | Gentelia et al. |
| 5,392,917 A | 2/1995 | Alpern et al. |
| 5,399,007 A | 3/1995 | Marconet |
| 5,417,246 A | 5/1995 | Perkins et al. |
| 5,425,730 A | 6/1995 | Luloh |
| 5,433,702 A | 7/1995 | Zelman et al. |
| 5,455,766 A | 10/1995 | Scheller et al. |
| 5,464,025 A | 11/1995 | Charles et al. |
| 5,508,836 A | 4/1996 | DeCaro et al. |
| 5,549,139 A | 8/1996 | Perkins et al. |
| 5,554,097 A | 9/1996 | Guy |
| 5,586,163 A | 12/1996 | Goldstein |
| 5,627,584 A | 5/1997 | Nishikori et al. |
| 5,685,877 A | 11/1997 | Pagedas et al. |
| 5,746,719 A | 5/1998 | Farra et al. |
| 5,779,053 A | 7/1998 | Partika et al. |
| 5,857,485 A | 1/1999 | Perkins et al. |
| 5,873,717 A | 2/1999 | Behringer |
| 5,910,110 A | 6/1999 | Bastable |
| 5,979,494 A | 11/1999 | Perkins et al. |
| 5,989,262 A | 11/1999 | Josephberg |
| 5,997,528 A | 12/1999 | Bisch et al. |
| 6,017,354 A | 1/2000 | Culp et al. |
| 6,022,088 A | 2/2000 | Metzler |
| 6,024,699 A | 2/2000 | Surwit et al. |
| 6,051,011 A | 4/2000 | Weidenbenner |
| 6,059,792 A | 5/2000 | Josephberg |
| 6,059,795 A | 5/2000 | Wallace et al. |
| 6,074,399 A | 6/2000 | Wallace et al. |
| 6,090,123 A * | 7/2000 | Culp ............... A61B 90/98 604/22 |
| 6,102,044 A | 8/2000 | Naidyhorski |
| 6,117,127 A | 9/2000 | Helmreich et al. |
| 6,158,437 A | 12/2000 | Vagley |
| 6,185,096 B1 | 2/2001 | Helot et al. |
| 6,206,014 B1 | 3/2001 | Cameron, III et al. |
| 6,217,584 B1 | 4/2001 | Nun |
| 6,251,113 B1 | 6/2001 | Appelbaum et al. |
| 6,258,111 B1 | 7/2001 | Ross et al. |
| 6,282,442 B1 | 8/2001 | Destefano et al. |
| 6,312,258 B1 | 11/2001 | Ashan |
| 6,329,778 B1 | 12/2001 | Culp et al. |
| 6,355,047 B1 | 3/2002 | Wallace et al. |
| 6,405,863 B1 | 6/2002 | Dhindsa |
| 6,428,487 B1 | 8/2002 | Burdorff |
| 6,508,823 B1 | 1/2003 | Gonon |
| 6,514,268 B2 | 2/2003 | Finlay et al. |
| 6,579,255 B2 | 6/2003 | Kadziauskas et al. |
| 6,602,227 B1 * | 8/2003 | Cimino ............ A61B 17/32006 604/113 |
| 6,616,606 B1 | 9/2003 | Peterson et al. |
| 6,623,500 B1 | 9/2003 | Cook et al. |
| 6,641,039 B2 | 11/2003 | Southard |
| 6,648,223 B2 | 11/2003 | Boukhny et al. |
| 6,666,875 B1 | 12/2003 | Sakurai et al. |
| 6,716,219 B1 | 4/2004 | Koch |
| 6,752,816 B2 | 6/2004 | Culp et al. |
| 6,769,546 B2 | 8/2004 | Busch |
| 6,773,445 B2 | 8/2004 | Finlay et al. |
| 6,896,141 B2 | 5/2005 | McMichael et al. |
| 6,945,981 B2 | 9/2005 | Donofrio et al. |
| 7,100,771 B2 | 9/2006 | Massengale et al. |
| 7,114,500 B2 | 10/2006 | Bonutti |
| 7,165,555 B2 | 1/2007 | Lee |
| 7,267,246 B2 | 9/2007 | Eiskant et al. |
| 7,331,463 B2 | 2/2008 | Hickey |
| 7,362,228 B2 | 4/2008 | Nycz et al. |
| 7,401,703 B2 | 7/2008 | McMichael et al. |
| 7,431,157 B2 | 10/2008 | Porret et al. |
| 7,517,351 B2 | 4/2009 | Culp et al. |
| 7,578,391 B2 | 8/2009 | Nakamura |
| 7,600,405 B2 | 10/2009 | Maurer, Jr. et al. |
| 7,604,007 B1 | 10/2009 | Wooley |
| D626,238 S | 10/2010 | Zinnanti |
| 7,900,805 B2 | 3/2011 | Shelton, IV et al. |
| 7,998,157 B2 | 8/2011 | Culp et al. |
| 8,002,783 B2 | 8/2011 | Vercellotti et al. |
| 8,038,692 B2 | 10/2011 | Valencia et al. |
| 8,080,029 B2 | 12/2011 | Charles |
| 8,177,064 B2 | 5/2012 | McCormick et al. |
| 8,177,776 B2 | 5/2012 | Humayun et al. |
| 8,187,293 B2 | 5/2012 | Kirchhevel |
| 8,312,800 B2 | 11/2012 | Turner et al. |
| 8,323,271 B2 | 12/2012 | Humayun et al. |
| 8,444,629 B2 | 5/2013 | Manna et al. |

(56) References Cited

U.S. PATENT DOCUMENTS

| | | |
|---|---|---|
| 8,496,681 B2 | 7/2013 | Easley |
| 8,525,059 B2 | 9/2013 | Berger et al. |
| 8,540,743 B2 | 9/2013 | Auld et al. |
| 8,545,529 B2 | 10/2013 | Underwood et al. |
| 8,568,391 B2 | 10/2013 | Kerns et al. |
| 8,623,000 B2 | 1/2014 | Humayun et al. |
| 8,728,108 B2 | 5/2014 | Gao et al. |
| 2001/0022615 A1 | 9/2001 | Fernandez et al. |
| 2002/0013517 A1 | 1/2002 | West et al. |
| 2002/0049454 A1* | 4/2002 | Whitman ........... A61B 10/0233 606/139 |
| 2003/0068596 A1 | 4/2003 | Castellini |
| 2003/0093503 A1 | 5/2003 | Yamaki et al. |
| 2003/0159969 A1 | 8/2003 | McMichael et al. |
| 2003/0165794 A1 | 9/2003 | Matoba |
| 2003/0178488 A1 | 9/2003 | Southard |
| 2003/0205233 A1 | 11/2003 | Aboul-Hosn et al. |
| 2004/0004019 A1 | 1/2004 | Busch |
| 2004/0024288 A1 | 2/2004 | Uchikubo |
| 2004/0034340 A1 | 2/2004 | Biscup |
| 2004/0036386 A1 | 2/2004 | Olivera |
| 2004/0116952 A1 | 6/2004 | Sakurai et al. |
| 2004/0138518 A1 | 7/2004 | Rise et al. |
| 2004/0139048 A1 | 7/2004 | Kerr, II et al. |
| 2004/0186683 A1 | 9/2004 | Farber et al. |
| 2004/0208780 A1 | 10/2004 | Faries, Jr. et al. |
| 2004/0243147 A1 | 12/2004 | Lipow |
| 2005/0128987 A1 | 6/2005 | Liang |
| 2005/0245888 A1 | 11/2005 | Cull |
| 2005/0283138 A1 | 12/2005 | Tashiro et al. |
| 2006/0002258 A1 | 1/2006 | Nakamura et al. |
| 2006/0046226 A1 | 3/2006 | Bergler et al. |
| 2006/0086634 A1 | 4/2006 | Steppe |
| 2006/0095066 A1 | 5/2006 | Chang et al. |
| 2006/0100497 A1 | 5/2006 | Sawazaki et al. |
| 2006/0109105 A1 | 5/2006 | Varner et al. |
| 2006/0119481 A1 | 6/2006 | Tethrake et al. |
| 2006/0140139 A1 | 6/2006 | DiSilestro et al. |
| 2006/0142739 A1 | 6/2006 | DiSilestro et al. |
| 2006/0240771 A1 | 10/2006 | Graves et al. |
| 2006/0244593 A1 | 11/2006 | Nycz et al. |
| 2006/0255938 A1 | 11/2006 | Van den Brink |
| 2006/0272979 A1 | 12/2006 | Lubbers et al. |
| 2006/0289016 A1 | 12/2006 | Kammer et al. |
| 2007/0258626 A1 | 11/2007 | Reiner |
| 2007/0282353 A1 | 12/2007 | Surti et al. |
| 2007/0290654 A1 | 12/2007 | Govari et al. |
| 2008/0030345 A1 | 2/2008 | Austin et al. |
| 2008/0041282 A1 | 2/2008 | Goschy et al. |
| 2008/0120137 A1 | 5/2008 | Nyholm |
| 2008/0125761 A1 | 5/2008 | Weston et al. |
| 2008/0146988 A1 | 6/2008 | Olivera et al. |
| 2008/0167644 A1 | 7/2008 | Shelton et al. |
| 2008/0200836 A1 | 8/2008 | Speeg et al. |
| 2008/0208233 A1 | 8/2008 | Barnes et al. |
| 2008/0272023 A1 | 11/2008 | McCormick |
| 2008/0281254 A1 | 11/2008 | Humayun et al. |
| 2008/0281301 A1 | 11/2008 | DeBoer et al. |
| 2008/0308698 A1 | 12/2008 | Steppe |
| 2009/0143734 A1 | 6/2009 | Humayun et al. |
| 2009/0248007 A1 | 10/2009 | Falkenstein et al. |
| 2010/0134303 A1 | 6/2010 | Perkins |
| 2010/0174415 A1 | 7/2010 | Humayun et al. |
| 2011/0042597 A1 | 2/2011 | Huculak et al. |
| 2011/0112518 A1 | 5/2011 | Stanton |
| 2011/0186456 A1 | 8/2011 | Bertazzoni |
| 2011/0190690 A1 | 8/2011 | Humayun et al. |
| 2011/0276340 A1 | 11/2011 | DeBoer et al. |
| 2011/0295193 A1 | 12/2011 | Fitzgerald et al. |
| 2012/0232540 A1 | 9/2012 | Baur et al. |
| 2013/0009606 A1 | 1/2013 | Smith et al. |
| 2013/0150875 A1 | 6/2013 | McDonell et al. |
| 2014/0238890 A1 | 8/2014 | Kerns et al. |
| 2014/0296900 A1 | 10/2014 | Barnes et al. |
| 2014/0323813 A1 | 10/2014 | Humayun et al. |
| 2014/0365235 A1 | 12/2014 | DeBoer et al. |
| 2014/0378952 A1 | 12/2014 | Humayun et al. |
| 2015/0144514 A1 | 5/2015 | Brennan et al. |
| 2015/0148615 A1 | 5/2015 | Brennan et al. |

FOREIGN PATENT DOCUMENTS

| | | |
|---|---|---|
| EP | 1236439 | 9/2002 |
| EP | 1236439 B1 | 1/2007 |
| EP | 1813199 | 8/2007 |
| EP | 1815798 A2 | 8/2007 |
| EP | 1815798 A3 | 10/2007 |
| EP | 2441393 | 4/2012 |
| GB | 1349881 | 4/1974 |
| JP | 05/044111 | 6/1993 |
| JP | 2004/250108 | 6/1993 |
| JP | 2002/515293 | 5/2002 |
| JP | 3310360 | 5/2002 |
| JP | 3088841 | 10/2002 |
| JP | 2004/081867 | 3/2004 |
| JP | 2005/046412 | 2/2005 |
| JP | 2006/511285 | 4/2006 |
| JP | 2007/501055 | 1/2007 |
| JP | 2007/020960 | 2/2007 |
| JP | 2009/219718 | 10/2009 |
| JP | 2010/503513 | 2/2010 |
| WO | 92/20310 | 11/1992 |
| WO | 95/01135 | 1/1995 |
| WO | 98/06338 | 2/1998 |
| WO | 99/59510 | 11/1999 |
| WO | 99/66444 | 12/1999 |
| WO | 2000/32115 | 6/2000 |
| WO | 2000/32123 | 6/2000 |
| WO | 01/12098 | 2/2001 |
| WO | 02/083021 | 10/2002 |
| WO | 03/034213 | 4/2003 |
| WO | 2004/060184 | 7/2004 |
| WO | 2004/105631 | 12/2004 |
| WO | 2005/016183 | 2/2005 |
| WO | 2008/036453 | 3/2008 |
| WO | 2008/131357 | 10/2008 |
| WO | 2008/152378 | 12/2008 |
| WO | 2009/156591 | 12/2009 |
| WO | 2010/030850 | 3/2010 |

OTHER PUBLICATIONS

Extended European Search Report for Patent Application No. 16196682.5, dated Feb. 16, 2017; 7 pages.

Extended European Search Report for Patent Application No. 16199915.6, dated Feb. 28, 2017; 6 pages.

International Preliminary Report on Patentability and Written Opinion dated Apr. 26, 2011 in PCT Application No. PCT/US2008/080832, filed Oct. 22, 2008.

International Preliminary Report on Patentability and Written Opinion dated Oct. 20, 2009 in PCT Application No. PCT/US2008/061058, filed on Apr. 21, 2008

International Search Report and Written Opinion dated Aug. 27, 2008 for PCT Application No. PCT/US2008/061058, filed on Apr. 21, 2008.

International Search Report and Written Opinion dated Dec. 22, 2008 in PCT Application No. PCT/US08/061065, filed in Dec. 21, 2008.

International Search Report and Written Opinion dated Jul. 29, 2010 in PCT Application No. PCT/US2008/080832, filed Oct. 22, 2008.

International Search Report and Written Opinion dated Jun. 2, 2011 in PCT Application No. PCT/US2011/020415 filed Jan. 6, 2011.

International Search Report and Written Opinion dated Oct. 18, 2012 for PCT Application No. PCT/US2012/034480.

International Search Report and Written Opinion dated Sep. 2, 2008 in PCT Application No. PCT/US2008/061043, filed Apr. 21, 2008.

Merriam-Webster.com definition of "tray"; http://www.merriam-webster.com/dictionary/tray, 2017.

Partial International Search Report dated Apr. 27, 2010 for PCT Application No. PCT/US2008/080832, filed Oct. 22, 2008.

(56) References Cited

OTHER PUBLICATIONS

Partial International Search Report dated Jul. 6, 2012 for PCT Application No. PCT/US2012/034480, filed Apr. 20, 2012.
Australian Office Action, Application No. 2015210377; 4 pages, dated Sep. 15, 2016.
Calhoun et al., "The Roto-Extractor in Pediatric Ophthalmology," Department of Pediatric Ophthalmology, Wills Eye Hospital and Stain Christopher's Hospital for Children, Philadelphia, PA, Tr. Am. Ophth. Soc. vol. LXXIII, 1975, 14 pgs.
Douvas et al., "Microsurgical Roto-Extractor Instrument for Vitrectomy," New Research on the Aetiology and Surgery of Retinal Detachment Mod. Probl. Ophthal., vol. 15, pp. 253-260 (Karger, Basel 1975); 8 pages.
Extended European Search Report for Patent Application No. 16189098.3, dated Jun. 21, 2017; 11 pages.
Extended European Search Report received in European Patent App. No. 08746468, dated Nov. 23, 2010.
Extended European Search Report, European Patent Application No. 15152563.1, 5 pages, dated Jul. 23, 2015.
International Preliminary Report on Patentability in PCT Application No. PCT/US2011/020415, dated Jan. 30, 2012.
International Preliminary Report on Patentability in PCT Application No. PCT/US2012/034480, dated Nov. 14, 2013.
International Preliminary Report on Patentability in PCT Application No. PCT/US2014/067717, dated Jun. 9, 2016; 12 pages.
International Search Report and Written Opinion in PCT Application No. PCT/US2014/067717, dated Mar. 5, 2015.
Invitation to Pay Additional Fees and Partial International Search Report in Application No. PCT/US2008/080832 dated Apr. 27, 2010 (DOHENY.009QPC); 2 pages.
Japanese Office Action, Application No. 2014-509305; with English translation; 6 pages, dated Sep. 2, 2015.
Japanese Office Action, Application No. 2015-108508; 6 pages with translation, dated May 16, 2017.
Japanese Office Action, Application No. 2015-108508; 8 pages with translation, dated Mar. 28, 2016.
Japanese Office Action, Application No. 2016-030648; 6 pages with translation, dated Feb. 28, 2017.
Office Action for Japanese Patent Application No. 2016-030648, dated Aug. 7, 2017; 5 pages, Aug. 6, 2017.
Office Action for Korean Patent Application No. 10-2012-7020831, dated Apr. 11, 2017; 5 pages.
Office Action, Chinese Patent Application No. 201180011864.8, 9 pages, dated Oct. 28, 2015.
Office Action, European Patent Application No. 12187535.5, 4 pages, dated Aug. 14, 2015.
Office Action, Korean Patent Application No. 10/2015-7020105, 5 pages, dated Aug. 27, 2015.
U.S. Appl. No. 13/084,478, including its prosecution history, and the Office Actions therein.
Office Action for Australian Patent Application No. 2017216458, dated Mar. 21, 2018; 2 pages.
Office Action for European Patent Application No. 16196682.5, dated Apr. 17, 2018; 4 pages.
Office Action for Canadian Patent Application No. 2924148, dated May 1, 2018; 5 pages.
Office Action for Indian Patent Application No. 7157/DELNP/2009 dated Jun. 14, 2018; 6 pages.

* cited by examiner

INDEPENDENT SURGICAL CENTER

CROSS-REFERENCE TO RELATED APPLICATIONS

This application is a continuation of U.S. patent application Ser. No. 14/092,159, entitled "Independent Surgical Center" and filed Nov. 27, 2013, which is a continuation of U.S. patent application Ser. No. 13/084,471, entitled "Independent Surgical Center" and filed Apr. 11, 2011, now U.S. Pat. No. 8,623,000, which is a continuation of U.S. patent application Ser. No. 12/107,038, entitled "Independent Surgical Center" and filed Apr. 21, 2008, now U.S. Pat. No. 8,177,776, which claims the benefit of U.S. Provisional Application No. 60/925,546, entitled "Independent Surgical Center Including A Portable Vitrectomy Handpiece And Infusion/Aspiration Cassette" and filed on Apr. 20, 2007. Each of the foregoing applications is hereby incorporated herein by reference in their entirety. U.S. patent application Ser. No. 12/107,038 is also related to U.S. application Ser. No. 12/106,962, now U.S. Pat. No. 8,177,064, and entitled "Surgical Pack and Tray", and U.S. application Ser. No. 12/107,052 and entitled "Personal Surgical Center", now abandoned, both filed on Apr. 21, 2008, and the foregoing applications are hereby incorporated herein by reference in their entirety.

FIELD

The present invention relates generally to surgical systems, and more particularly to a surgical system including instrumentation that is operable without an external control console.

BACKGROUND

Innovations in medical surgery have allowed many to recover from ailments previously thought untreatable or incurable. For example, various ophthalmic surgical procedures have been developed which repair portions of the human eye, including internal components of the eye, to relieve different visual ailments. As medical surgery develops and expands into new areas of the human body, often with limited accessibility, more complex surgical instrumentation is developed. Furthermore, the more complex the surgical instrumentation, generally the greater demand there is for precision of the surgical instrumentation.

To increase precision and accuracy in surgical procedures, control consoles are often integrated into surgical systems. Control consoles may be used, for example, to adjust the control parameters of the various surgical instruments being used, to monitor the status of the surgical instruments, and to perform rapid calculations and provide feedback to doctors and other medical personnel to assist in determining how to proceed with the surgical procedure. Ophthalmic surgical procedures are no different. For example, a vitrectomy, which involves the surgical removal of fluid within the eye, is generally performed using instrumentation driven by a computer system housed in a large control console. The control console is generally stationary or housed in a large rolling unit outside the sterile barrier, and includes device modules which directly connect to the surgical instrumentation. With the control console located outside the sterile barrier, the surgeon or other qualified practitioner operates the instrumentation at the patient level, while at least one other medical personnel operates the controls at the control console at the direction of the surgeon.

SUMMARY

Embodiments of the present invention are directed to an independently operable surgical system for conducting surgeries and medical procedures, such as, for example, vitrectomies and other ophthalmic surgical procedures.

According to one embodiment of the invention, an independent system for a surgical procedure is comprised of a control device including a processing unit; and a plurality of instruments associated with the surgical procedure and operably coupled to the control device, wherein the control device and the plurality of instruments are prepackaged together, and the processing unit is configured to control at least one of the prepackaged instruments. The instruments may be electrical instruments.

According to another embodiment of the invention, a surgical system is comprised of a portable surgical tray including a processing unit; a plurality of instruments operably coupled to the processing unit; and a user input device providing a user input for controlling an operating parameter of one or more of the plurality of instruments, wherein the processing unit is configured to receive the user input and transmit an operating command to the one or more of the plurality of instruments.

In yet another embodiment of the invention, a self-powered surgical system for a surgical procedure is comprised of a surgical tray; a plurality of handheld instruments; a power source in at least one of the surgical tray and a handheld instrument; and a processing unit, wherein the processing unit is configured to execute program instructions, the program instructions including instructions for: detecting power from the at least one power source; directing power to the plurality of handheld instruments from at least one power source; and establishing communication with each of the plurality of handheld instruments.

According to one embodiment, a portable biological cutting and aspiration device includes: a cutting tip; a fluid aspiration device; and an integrated control unit coupled to the cutting tip and fluid aspiration device, wherein the control unit is configured to control cutting and aspiration of the cutting tip and fluid aspiration device.

According to one embodiment, a portable infusion and aspiration device includes: an aspiration chamber; an aspiration line coupled to a biological tissue cutting and aspiration device, the aspiration line configured to suction matter dislodged from a surgical site into the aspiration chamber; an infusion chamber having an infusion solution; an infusion line coupled to the infusion chamber and configured to inject the infusion solution to the surgical site for maintaining pressure in the surgical site, wherein the aspiration chamber and infusion chamber are included in a single, disposable cassette.

DETAILED DESCRIPTION

Figure 1:
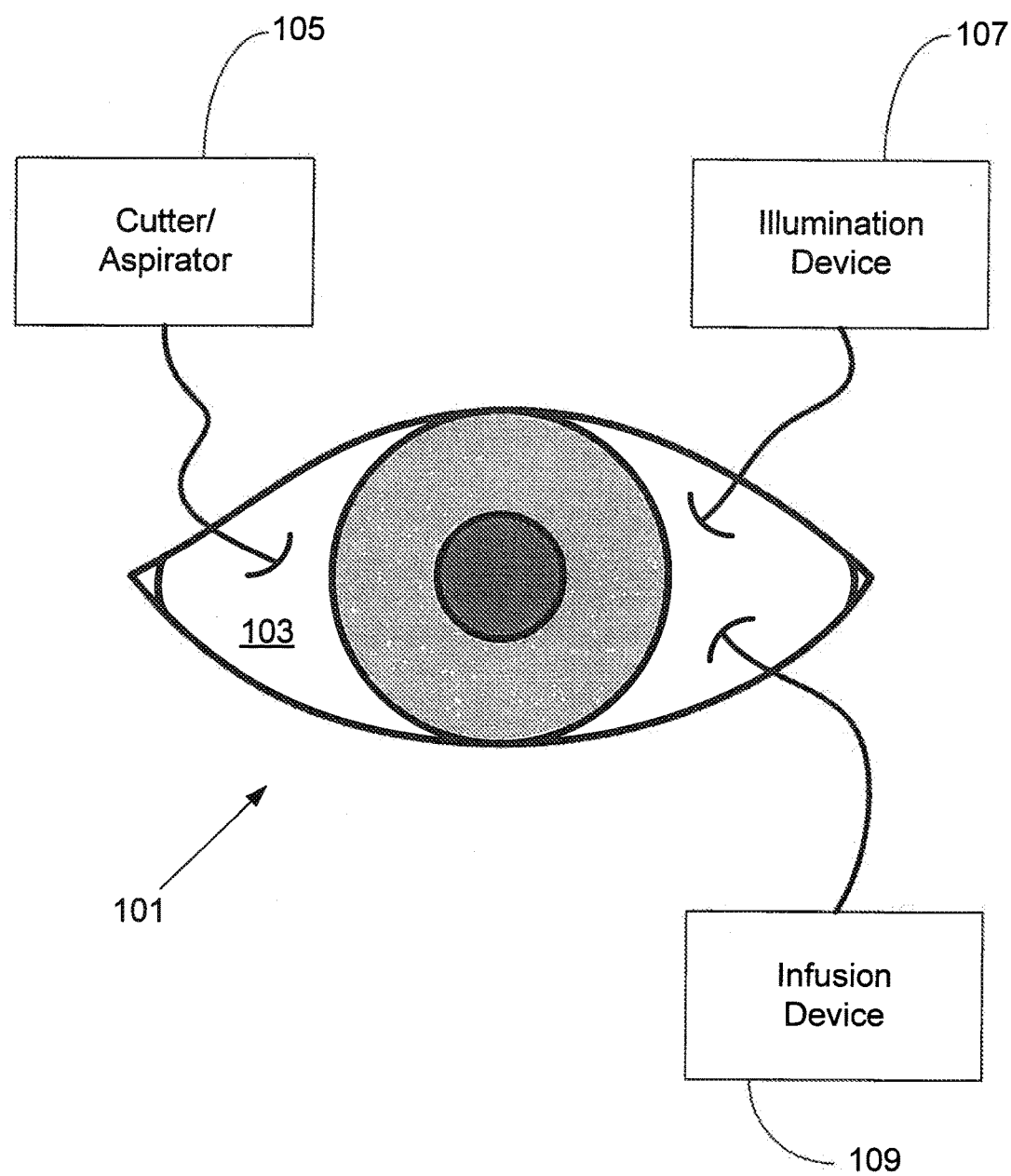
FIG. 1 is a block diagram of various instruments inserted into the eye in the course of performing a vitrectomy.

FIG. 1 is a block diagram of various instruments inserted into the eye in the course of performing a vitrectomy. Vitreous is a normally clear, gel-like substance that fills the center of the eye, for example, eye 101. In some instances, blood, debris, or scar tissue may collect in the vitreous, partially or fully obstructing vision. In these instances, a vitrectomy, or surgical removal of all or a part of the eye's vitreous, may be performed.

To perform a vitrectomy, a number of incisions are made into the sclera 103, the white portion of the eye. Various instruments access the center of the eye through the incisions. The inserted instruments in FIG. 1 include a handheld biological tissue cutter and fluid aspiration tool ("handpiece") 105, an illumination device 107, and an infusion device 109. The handpiece includes a biological tissue cutter for cutting or dislodging portions of the eye's vitreous, as well as an aspirator for removal of the cut or dislodged portions. The infusion device is used to replace fluid and maintain proper pressure in the eye. The illumination device is used as a light source to see into the center of the eye during the procedure.

The present invention is directed to an independent surgical system operable without the use of an external surgical console. In some embodiments, for example, a modular surgical system consists of independent surgical instrumentation. The surgical instrumentation may include, for example, a series of interlinked handheld instruments, such as the cutting handpiece and the illumination device. In some embodiments, the individual instruments contain self-sustaining operating intelligence and are not dependent on commands from a control source, providing a surgeon or other medical practitioner with full and independent control of each individual instrument within a sterile field.

Although the independent surgical center is described herein mainly in connection with vitrectomy procedures, a person of skill in the art should recognize that the center may also be configured for other medical procedures performed on all tissue including the eye or other parts of the human body. For example, phacoemulsification involves the removal of a lens of an eye using a similar handpiece including an ultrasonic cutter and an aspirator. For various other applications, instruments may include, for example, different cutters, vacuuming devices, irrigation devices, viewing devices, and/or illumination devices, among others. According to one embodiment of the invention, most, if not all, of the instruments of a particular system contain the circuitry and power to control and operate themselves independently of each other. In some embodiments, the instruments may communicate with each other via a wireless connection, and one instrument may act as a main processing or control unit. Therefore, while the description may often refer to details of embodiments of the invention configured for a vitrectomy, the description is not intended to represent the only application in which the invention may be utilized. While different procedures may involve slightly different embodiments, it is to be understood that equivalent functions and structures may be realized by the different embodiments that are also intended to be encompassed within the spirit and scope of the invention.

Figure 2A:
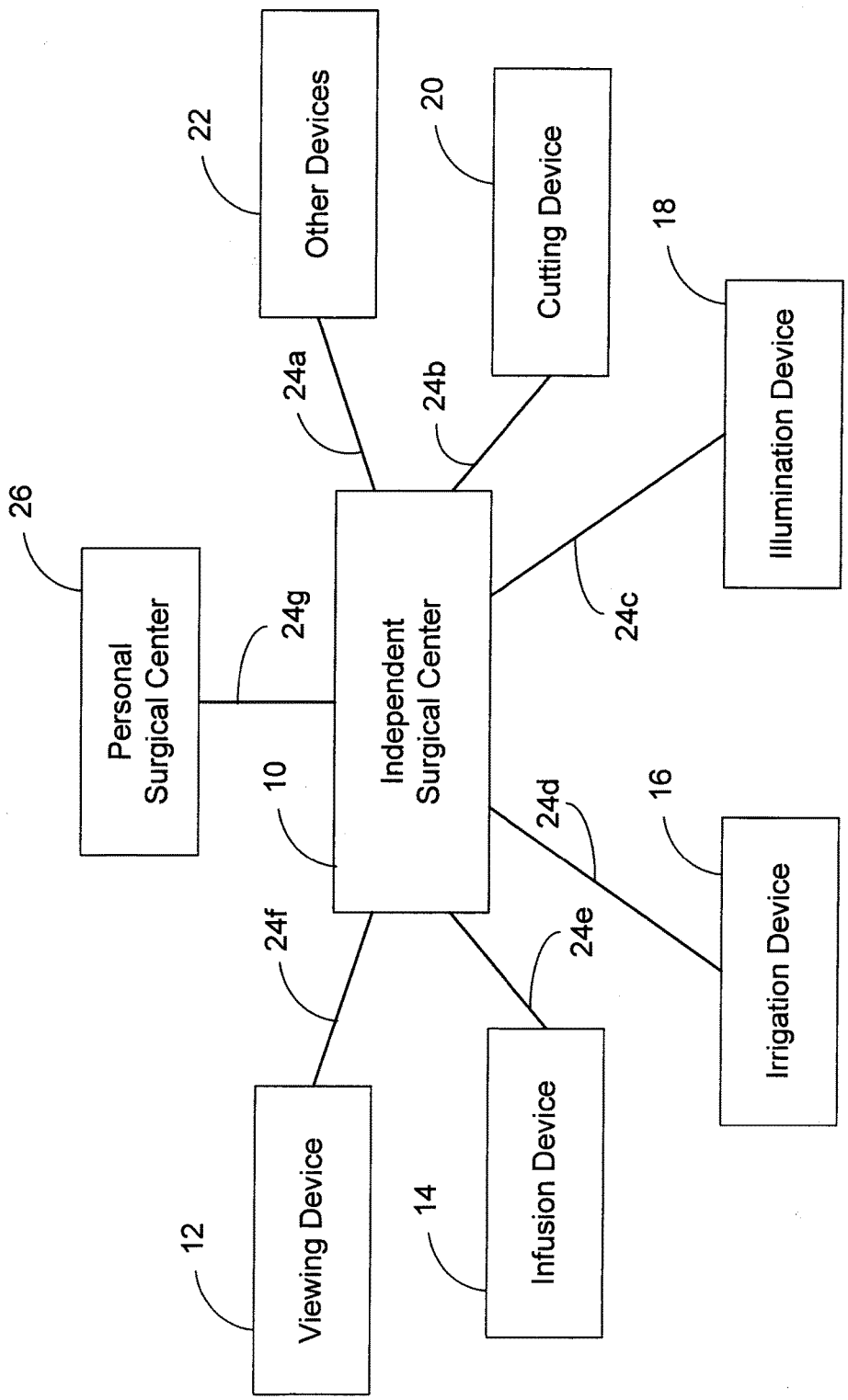
FIG. 2a is a block diagram of a surgical system including an independent surgical center 10 according to one embodiment of the invention.

FIG. 2*a* is a block diagram of a surgical system including an independent surgical center 10 according to one embodiment of the invention. The independent surgical center 10 acts as a control device for the surgical system and is operably coupled to one or more medical instruments, such as, for example, one or more viewing devices 12, infusion devices 14, irrigation devices 16, illumination devices 18, and cutting devices 20, over wired or wireless connections 24*f*, 24*e*, 24*d*, 24*c*, 24*b*. The independent surgical center 10 is also operably coupled to other devices 22 over wired or wireless connection 24*a*. Such other devices may include, but are not limited to, foot pedals, secondary display screens, audio outputs, and the like.

According to one embodiment of the invention, the independent surgical center 10 is further optionally coupled to a personal surgical center over connection 24*g*. Preferably, connection 24*g* is a wireless connection, although the connection may alternatively take the form of a wired connection. As described in detail in U.S. application entitled Personal Surgical Center filed on even date herewith, the personal surgical center 26 is configured to monitor the settings of the various medical instruments while the actual control of the medical instruments is via the independent surgical center 10 and/or via logic and circuitry included in the medical instrument themselves. In this regard, the independent surgical center 10 and medical instruments 12-20 are located within the sterile field in which a surgery is performed, while the personal surgical center 26 is located outside the sterile field. In this manner, the surgeon has direct access and control of the independent surgical center 10 and instruments during surgery.

The various connections 24*a*-24*g* from the independent surgical center 10 may be wired or wireless. A wireless connection may be, without limitation, a wireless local area connection, such as, for example, an 802.11 connection, a personal area network connection such as, for example, Bluetooth, or any other radio or cellular connection conventional in the art. A wired connection may be, for example, a serial bus, parallel bus, Ethernet connection, or the like. For example, connection 24*b* between the cutting device 20 and the independent surgical center 10 may be a wired connection. In addition, infusion and aspiration lines may connect the infusion device and irrigation device to the independent surgical center 10 and/or the cutting device 20.

The independent surgical center 10 includes the circuitry, power, and logic to drive and control one or more of the medical instruments. According to one embodiment of the invention, the independent surgical center 10 is embodied as a surgical tray. According to another embodiment of the invention, the independent surgical center is embodied as a particular medical instrumentation such as, for example, an infusion/aspiration cassette. According to this latter embodiment, the particular medical instrumentation not only has the logic and circuitry to control itself, but also acts as a control center to control the functionality of some or all of the other instruments.

Figure 2B:
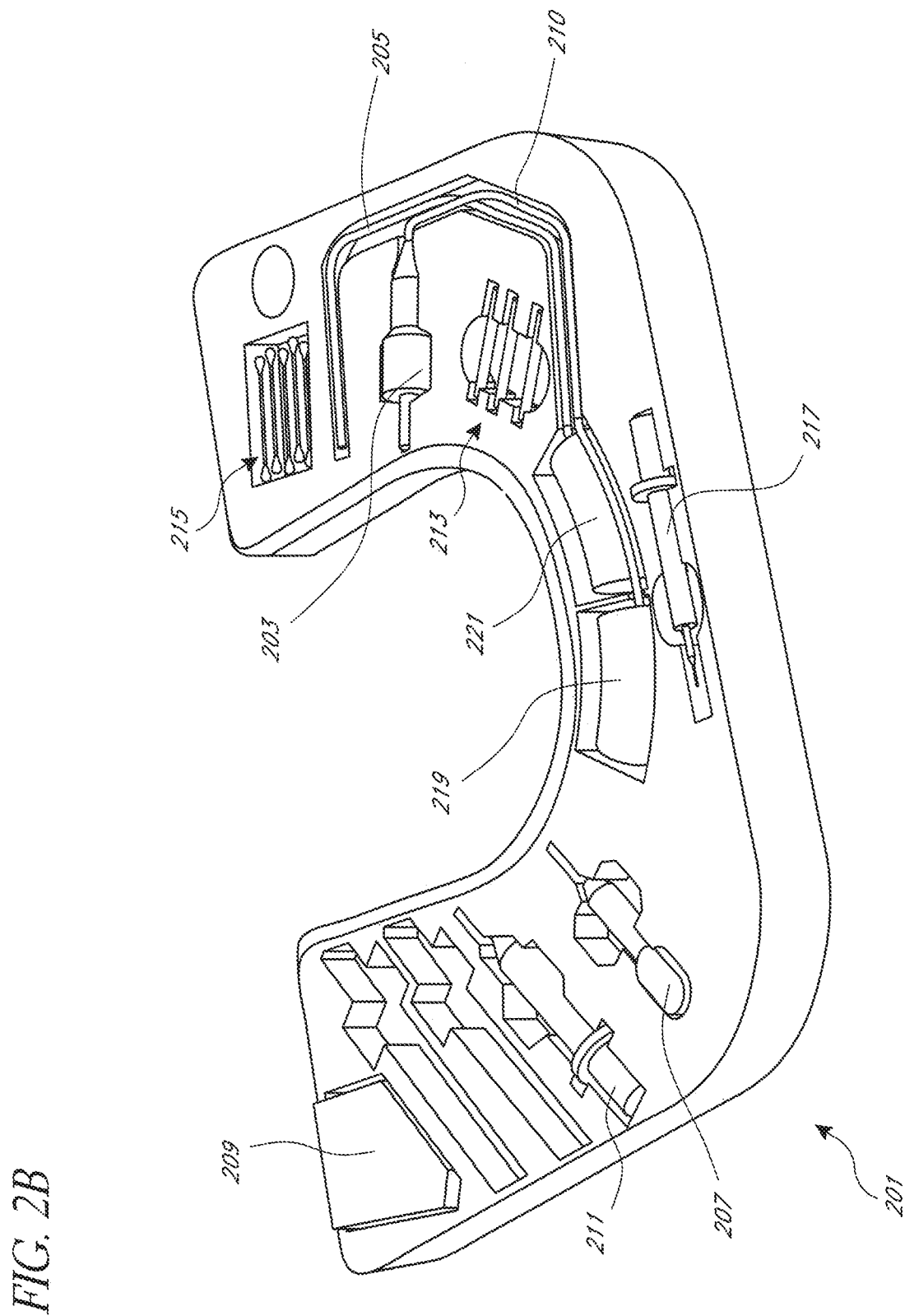
FIG. 2b is a schematic illustration of an independent surgical center embodied as a surgical tray in accordance with one embodiment of the invention.

FIG. 2b is a schematic illustration of an independent surgical center embodied as a surgical tray in accordance with one embodiment of the invention. In the embodiment illustrated in FIG. 2, the surgical tray 201 houses and controls various medical instruments which may be associated with different surgery procedures. In some embodiments, the surgical tray of FIG. 2 provides a sterile environment for packaging of the individual instruments before, and in some instances after, a procedure is performed. In some embodiments, the tray, and the instruments held in the tray, are designed to be discarded after a single use.

In the embodiment illustrated in FIG. 2b, the tray houses various removable handheld instruments and surgical supplies, including a handpiece 203, an infusion line 205, an illumination device 207, a speculum 209, a syringe 211, cannulas 213, Q-TIPS® cotton swabs 215, and a supply of artificial tears 217. The tray also houses a cartridge including an aspiration chamber 219, an infusion chamber 221, and a pump or similar device for each respective chamber. In the embodiment illustrated in FIG. 2b, the handpiece is coupled to the aspiration chamber 219 via aspiration line 210, and to the infusion chamber 221 over the infusion line 205.

According to one embodiment of the invention, the tray is in wired or wireless communication with one or more pieces of surgical instrumentation housed in the tray that require power or control from the tray. The tray may also be in wireless communication with other devices not housed in the tray, for example, a foot pedal, and/or an external monitor. The tray may act as a communication medium between each of the instruments of the surgical system. In embodiments where the tray communicates with an external monitor, the entire system generally remains independently operable, with the monitor typically serving only in a data collection, display and storage capacity.

According to one embodiment of the invention, the various medical instruments, including the tray, are designed to be portable, lightweight, and inexpensive. In some embodiments, the tray includes internal circuitry and various components for controlling the various medical instruments. Internal components may include, for example, a processing unit, user controls, a power source, and a plurality of different interfacing devices. The processing unit may be, for example, a microprocessor based unit, and ASIC, or the like. The interfacing devices may include, for example, a wireless communication interface to communicate with the other instruments of the surgical system. The power source, for example, a battery, allows the tray to be independently powered, and in some embodiments, provide power to devices connected to the tray, such as the handpiece. In some embodiments, the tray may also include a display or speaker, which may output various status indicators or settings of connected instruments.

In some embodiments, the tray is designed for a single use, and the instruments of the tray are prepackaged together in sterile packaging. In these embodiments, the packaging may be opened, and the tray and the components within the tray, activated, within a sterile operating field just prior to performing the surgical procedure. This gives a medical practitioner access to and control of all the applicable surgical instrumentation within the sterile field, including any instrument controls and status indicators located on the tray. In some embodiments, upon activation, the tray may perform an initial scan or similar information retrieval process, to determine the available devices or instruments with which it may communicate during the procedure. The tray may establish lines of communication, generally wirelessly, with the various different instruments of the tray.

According to one embodiment of the invention, the tray is connected to the handpiece 203 and the infusion line 205. In biological tissue cutting applications, the handpiece may include a biological tissue cutter, and may be connected to the tray via the fluid aspiration line 210. In operation, the cutter cuts or dislodges biological tissue, and the aspiration line suctions the dislodged tissue, where it is collected in the isolated aspiration chamber 219. The infusion line 205 may be used to inject the surgical site with fluid or gaseous solutions or other materials to replace the aspirated tissue. For example, in vitrectomies, pressure is maintained within the eye through infusion of balanced salt solution to replace the aspirated vitreous. Infusion fluids may be held in an infusion chamber of the tray, or alternatively in a sealed infusion bag or pouch held in the infusion chamber, and infused into a patient through the infusion line at a rate determined by controls located on the tray. According to one embodiment of the invention, both the aspiration chamber 219 and infusion chamber 221 reside in a single disposable cassette.

In some embodiments, operating parameters for the different instruments, for example, cut speed, aspiration pressure, infusion rate, and illumination level, may be controlled directly through the individual devices used to perform each respective function. For example, the handpiece may include controls for controlling the cut speed and the aspiration pressure, providing a surgeon more direct control over the procedure. Alternatively, input devices coupled to the tray be used to control the parameters of one or more of the medical instruments. An exemplary input device is a foot pedal wirelessly connected to the tray. A surgeon may use the foot pedal to control, for example, the cut speed and aspiration pressure. The tray receives the changes to the cut speed and/or aspiration pressure, and in turn controls the handpiece based on the received input. Similarly, the illumination level may be controlled directly on the illumination device, and the infusion rate may be controlled either by controls located on the infusion line or on the tray. A person of skill in the art should recognize that other input devices such as knobs, switches, and/or buttons may be used for control input in addition or in lieu of the foot pedal.

The tray may also communicate with the various instruments to retrieve status information, for example, instrument settings, current operating parameters, and fault conditions, from the various instruments. For example, while the illumination device is wholly separable from the tray, and may function and be controlled independently of the tray, the tray may nevertheless receive information on the current illumination level and communicate that information to the surgeon or practitioner. According to one embodiment of the invention, the tray forwards the monitored information to the personal surgical center 26 over data communications link 24g. In some embodiments, information may be displayed on a built-in display mounted on the tray. In other embodiments, other output or user feedback means may be incorporated, for example, a series of LEDs indicating current parameter or status information of the various instruments.

Figure 3:
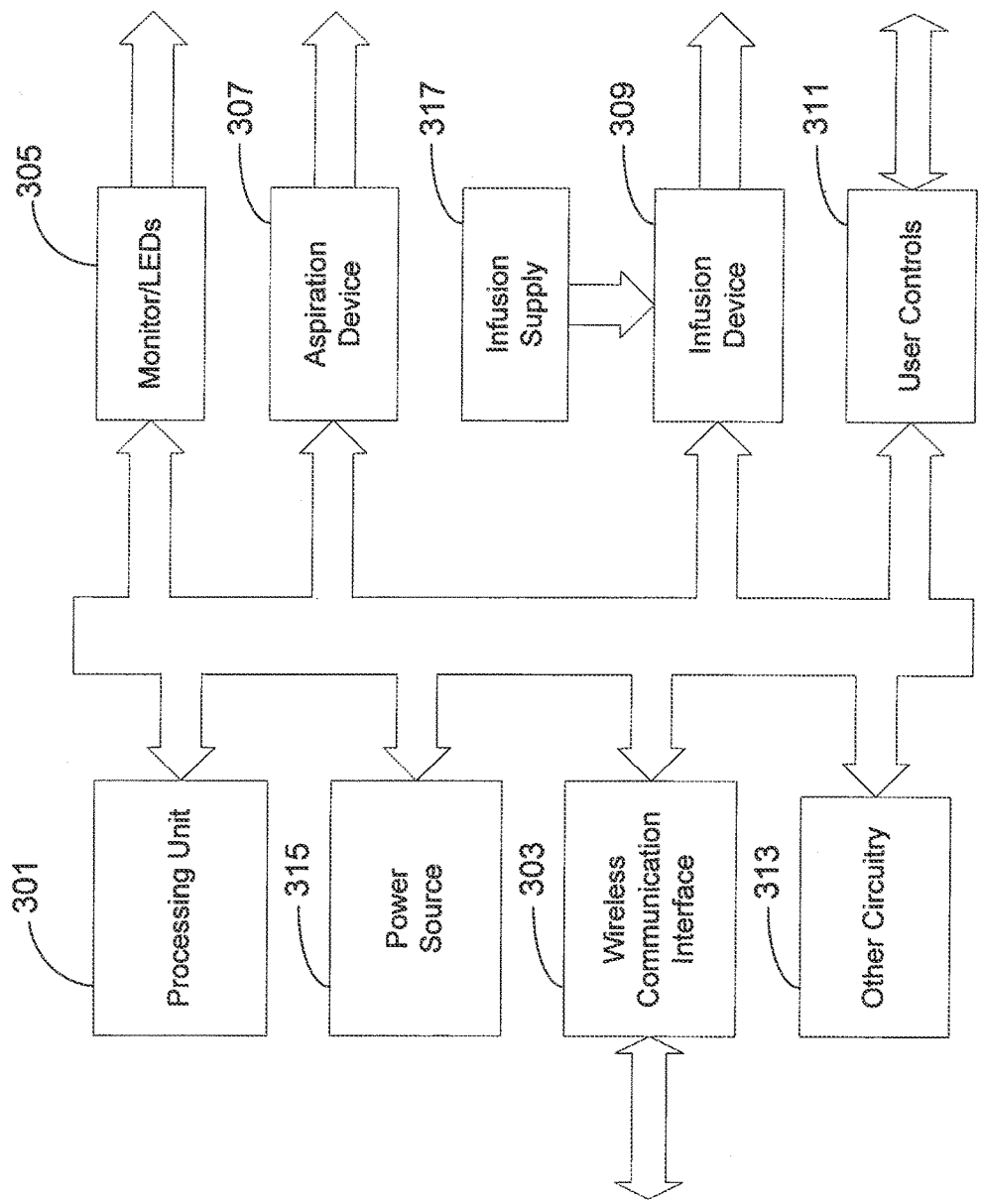
FIG. 3 is a block diagram of the internal components of an independent surgical center in accordance with one embodiment of the invention.

FIG. 3 is a block diagram of the internal components of an independent surgical center 10 in accordance with one embodiment of the invention. According to the illustrated embodiment, the independent surgical center 10 includes a processing unit 301 connected and in communication with a wireless communication interface 303, a status indicator such as a monitor or collection of LEDs 305, an aspiration device 307, an infusion device 309, a plurality of user controls or other input devices 311, and other components or circuitry 313. A power source 315 may also be connected to the various components, and provides power to run the other components. The infusion device may be further connected to a supply of infusion fluid or gas 317, for example, a reservoir of balanced salt solution.

The processing unit 301 facilitates operation of one or more instruments by sending control commands to those instruments, and acts as an information resource by collecting current parameter settings and other status information from the same or other instruments of the surgical system. In some embodiments, status information is collected from all of the connected instruments and communicated by the tray to a surgeon or other user of the surgical system, as well as optionally to the personal surgical center 26.

The processing unit 301 may control the medical instruments based on user requests. In some instances, the requests may come from user controls located on the independent surgical center itself, in the form of, for example, buttons or adjustable dials. In other instances, user controls may be received from connected devices, for example, the handpiece or the infusion line as illustrated in FIG. 2b. In still other instances, control or adjustment requests may be received from remote instruments of the surgical system, for example, the illumination device 18, or for example, a foot pedal, via the wireless communication interface 303.

The processing unit 301 processes the user requests and generates command signals to send to the instruments or devices for which the adjustments were intended. In some embodiments, the independent surgical center 10 may be configured to direct or control the operation of particular devices in the surgical system. For example, in the embodiment of the tray as the independent surgical center, the tray may be limited to controlling devices located on or within the tray itself, such as, for example, the aspiration device 307 and the infusion device 309. In some other embodiments, the processing unit 301 may serve as a central control unit for the various instruments and devices in the surgical system, and may receive all the instrument adjustment requests and send associated control commands to the appropriate devices in the system.

In operation, a user request may be received from a first device, for example, the handpiece, and be intended for adjusting a second device, for example, the aspiration device. The processing unit 301 may directly adjust the control parameters of the aspiration device, which may be, for example, a centrifugal pump, a venturi pump, a peristaltic pump, or any suitable vacuum based system, or may alternatively be a motor controlling a syringe or piston to apply vacuum pressure. Similar adjustments may be made to a connected infusion device, which may be, for example, a general disposable pump, peristaltic pump, a Harvard apparatus syringe pump, a spring loaded syringe, or an IV pole. In some embodiments, a supply of infusion solution is prepackaged with the system, the solution being appropriate for the particular application for which the system is intended. In vitrectomy procedures, the prepackaged solution may be sterile balanced salt solution. If a pump is used, it may pressurize the infusion chamber holding the balanced salt solution, causing the solution to enter the eye. Alternatively, a separately sealed infusion bag holding the balanced salt solution may be housed by the infusion chamber and connected to the infusion line. The pressure level of the infusion chamber may be increased, compressing the infusion bag, and forcing the balanced salt solution out of the infusion bag to the eye.

Some surgical procedures may involve gas exchange, or a combination of liquid and gas exchange. In some embodiments of the invention, the infusion device 309 may provide for multiple infusion sources, and hold various types of liquids and gases for infusion. In these embodiments, the independent surgical center 10 may also include a control which determines the infusion source being applied in the surgical procedure. For example, for a surgical system including an infusion source with a liquid solution and an infusion source with an air fluid or gaseous matter, the independent surgical center 10 may provide for a control to select between liquid solution exchange or air fluid exchange.

According to one embodiment of the invention, the independent surgical center also provides feedback to users in the form of setting monitors and status indicators. The processing unit 301 receives status information from the plurality of connected instruments, typically performed through data communication lines for connected instruments, or through the wireless communication interface for remote instruments. The processing unit compiles the information and communicates the information to the surgeon or other user. According to one embodiment of the invention, the independent surgical center may include a small monitor or screen for displaying information about the surgical procedure or the instrumentation. In addition to, or in lieu of, a monitor, optical LEDs and/or audio speakers may be provided to generate status outputs or alerts for various system events.

Figure 4:
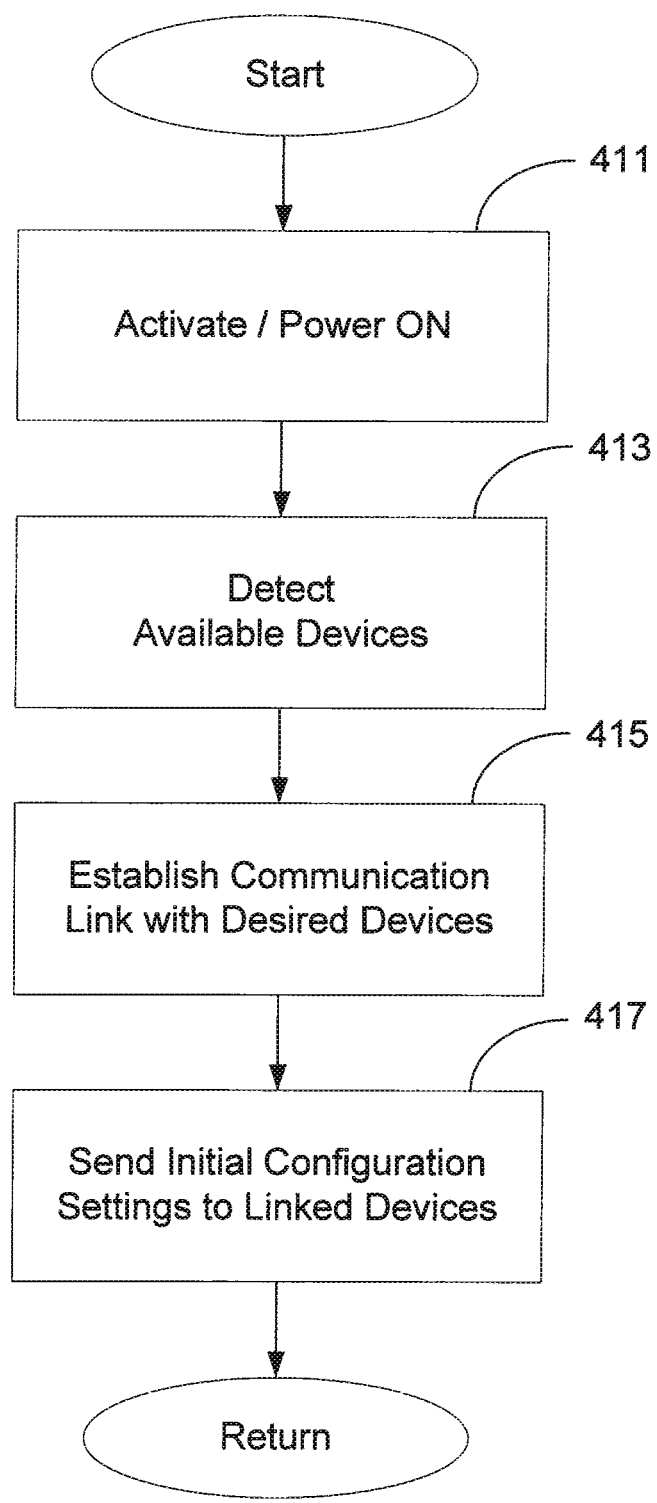
FIG. 4 is a flow diagram of an initialization and communication establishment process for an independent surgical center in accordance with one embodiment of the invention.

FIG. 4 is a flow diagram of an initialization and communication establishment process for an independent surgical center in accordance with one embodiment of the invention. The process may be implemented as computer program instructions stored in memory (not shown) and invoked by the processing unit 301. In some embodiments, the process of FIG. 4 is performed when the system is initialized. In block 411, the process activates or begins supplying power to the processing unit 301. In some embodiments, the independent surgical center 10 housing the processing unit also houses the power source 315 to supply power to the processing unit. Some embodiments may involve plugging the system into an external power source, for example, an electrical outlet. However, embodiments including an internal power source, for example, a battery, generally provide for better maneuverability. In embodiments where the power source is housed in the tray of the system, the power source may also power the aspiration and infusion devices 307, 309, and may provide power to a connected handpiece as well. In some embodiments where the independent surgical center 10 is embodied as the surgical tray, power to the independent surgical center 10 is activated once the tray is opened or removed from its packaging, through an automated switch activation or similar mechanism. The processing unit detects power from the power source and activates the system. In other embodiments, an additional user-controlled switch or control device may be provided to manually activate the power supply.

In block 413, the process detects one or more devices or instruments which may be utilized during a procedure in which the independent surgical center is used. In this regard, the process invokes the wireless communication interface 303, such as, for example, a radio frequency identification (RFID) reader, and automatically interrogates one or more identification tags, such as, for example, an RFID, tag coupled to the one or more devices or instruments or to packaging holding individual or multiple ones of the devices or instruments. The RFID tag transmits identification information (e.g. device ID or model number) as well as specific information on the individual instruments, for example, instrument types, configuration parameters, and available power settings. In some embodiments, some instruments may be included in surgical packages including specific surgical instrumentation associated with a particular procedure. In this embodiment, the packages may include RFID systems that identify the instruments in the package, or alternatively, each of the available instruments may include a separate RFID tag, so that communication may more readily be established with each of the individual devices. In some embodiments, for example, the embodiments described with respect to FIG. 2a, the surgical tray may include instruments which may be used for various different procedures. In these embodiments, the system may be configured to provide for selection of a desired procedure, and the tray may identify each available instrument to determine whether each instrument is to be used for the desired procedure.

In block 415, the process establishes communication with the one or more identified devices. The communication may then be used to control operation of the identified devices and/or to receive status information from the identified devices. According to one embodiment of the invention, wireless communication may not need to be established with all identified devices. For example, the process may be configured to select the instruments which are to be used in a particular procedure in response to a user command, and establish wireless links with those instruments, rather than with all the available instruments. In some embodiments, the processing unit first directs a power source to supply power to a selected instrument before communication may be established between the processing unit and the selected instrument.

In block 417, the process sends initial configuration settings to the devices with which communication has been established. Wireless data received from the various connected instruments may be used to, for example, pull up and configure the appropriate setup or monitoring screens on the independent surgical center itself, an external status monitor coupled to the independent surgical center, and/or on the personal surgical center. In some embodiments, the wireless connection may also be used to relay initial surgical settings and instrument fault parameters to one or more of the individual instruments. In some embodiments, each independent surgical center may be pre-configured to perform a specific procedure, and the processing unit 301 may send initial configuration settings to the one or more instruments based on the preconfigurations for a particular procedure. In some embodiments, the personal surgical center may invoke the user controls 311 reading or inputting user preferences or patient data or statistics. In these embodiments, initial configuration settings may instead be based on more user-specific or patient-specific information provided via the user controls.

Figure 5:
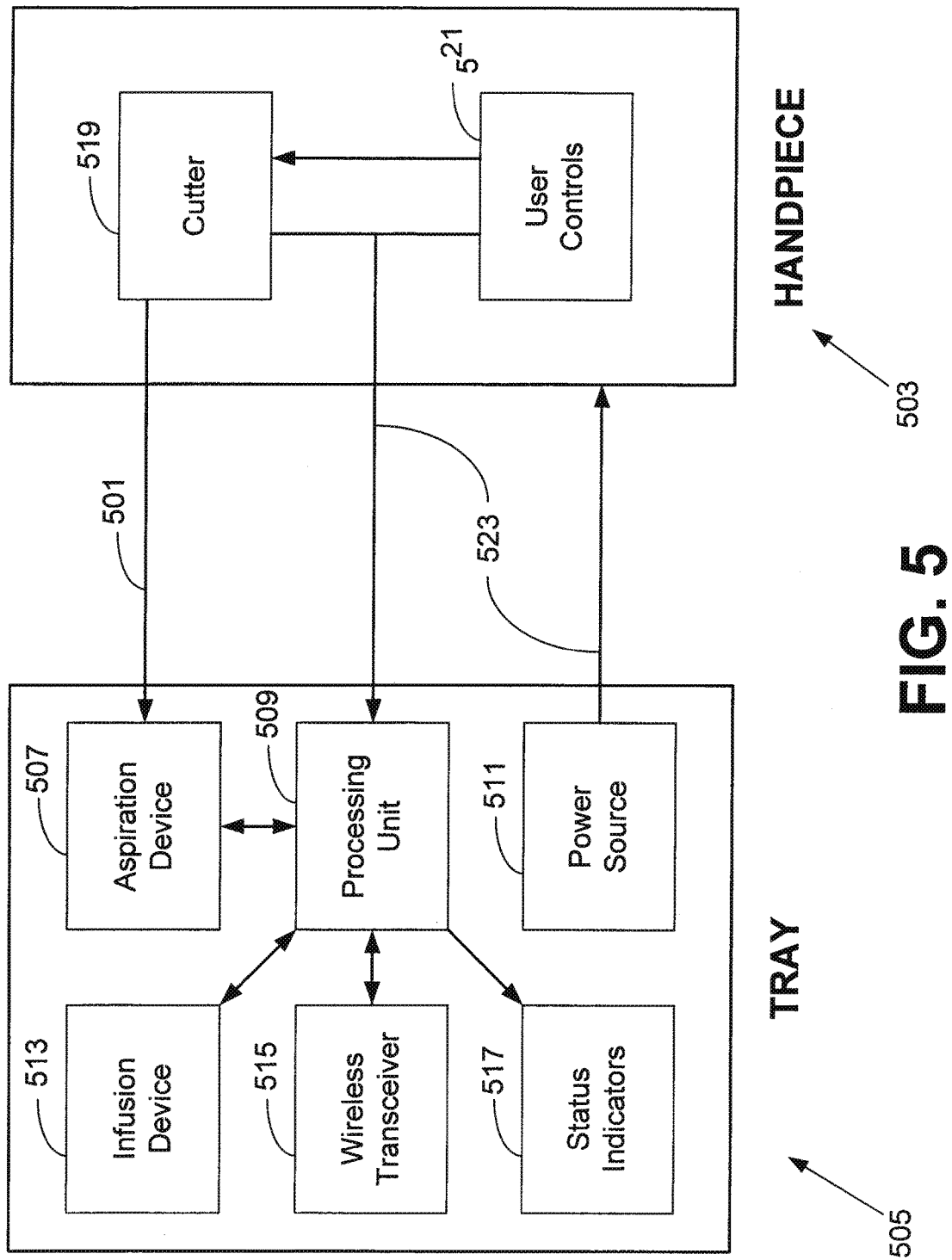
FIG. 5 is a block diagram of an independent surgical center embodied as a surgical tray in communication with a handpiece in accordance with one embodiment of the invention.

FIG. 5 is a block diagram of an independent surgical center embodied as a surgical tray 505 in communication with a handpiece 503 in accordance with one embodiment of the invention. According to this embodiment, the handpiece is a biological tissue cutting and fluid aspiration system. An aspiration line or tube 501 connects the handpiece 503 to the tray 505 for suctioning unwanted materials from a surgery site. In this regard, the tray includes an aspiration chamber and an aspiration device 507, for example, a pump or vacuum. In these embodiments, the aspiration device provides suction or vacuum to the handpiece through the aspiration line 501, and a reservoir or like chamber is provided for collection of materials aspirated through the line or tube. The aspiration chamber may be similar to the aspiration chamber 219 of FIG. 2b.

In alternative embodiments, the aspirating handpiece may be configured with an internal pump and collection chamber. According to these alternative embodiments, the aspiration line 501 would no longer be necessary, and the connection between the handpiece and the tray would be completely wireless.

In the embodiment illustrated in FIG. 5, in addition to the aspiration device 507, the tray includes a processing unit 509, a power source 511, an infusion device 513, a wireless transceiver 515, and status indicators 517. The processing unit 509, power source 511, infusion device 513, wireless transceiver 515, and status indicators 517 may be similar to the processing unit 301, power source 315, infusion device 309, wireless communication interface 303, and monitor/LEDs 305 described with respect to FIG. 3. The handpiece 503 includes a biological tissue cutter 519 and a set of user controls 521. In various embodiments of the invention, the components in the tray and the handpiece may be arranged differently. There may also be different combinations of components, including various components not included in FIG. 5, which may be included in other embodiments of the invention, depending on the application of each respective system.

The user controls 521 included in the handpiece may, for example, control the cut speed of the cutter on the handpiece, or for example, the aspiration level of the aspiration device, located on the tray, or both. Generally, user controls associated with a particular instrument or component of the system are located on that particular instrument or component, providing intuitive device control associations and easier access to users of the system. The user controls on the handpiece may be connected to and operate in accordance with the processing unit 509. The handpiece may also receive additional instructions or operation parameters, for example, a maximum permissible cut speed from the processing unit. The cutter 519 may communicate with the processing unit as well, for example, for relaying status information on the current cut speed. Furthermore, the power source 511 FIG. 5 is housed in the tray, providing power to the components of the tray. An electrical line 523 may be tethered from the tray to the handpiece, to facilitate communication between the handpiece and the tray, as well as supplying power to the components of the handpiece.

The aspiration device 507 housed on the tray may be one of various different aspirating instruments, for example, a centrifugal pump, or an alternate suitable vacuum based system. Some embodiments of the invention may provide controls for the aspiration device on the handpiece, while other embodiments may instead provide controls for the aspiration device on the tray. Still other embodiments of the invention may provide controls for the aspiration device on another instrument, for example, a foot pedal, in wireless (or wired) communication with the tray. The processing unit 509 retrieves aspiration adjustment requests from one of the various controls, and applies the adjustments to the aspiration device 507. The adjustments may cause the aspiration rate of the aspiration line, and consequently the aspiration rate of the handpiece, to fluctuate.

The infusion device 513 housed on the tray is typically connected to an outgoing infusion line (not shown). The infusion device may be one of various different infusion instruments, for example, a Harvard Apparatus syringe pump, or for example, a spring loaded syringe. The infusion device supplies different fluids or gases to a surgical site through the infusion line, the particular fluid or gas dependent on the particular surgical procedure being performed. In vitrectomies, for example, a sterile balanced salt solution is provided to the eye by the infusion device. In some embodiments, the infusion rate of the infusion device may be controlled by the processing unit 509 of the tray based on, for example, the rate of aspiration. In some applications, the infusion rate may be in synchrony with the aspiration rate, to maintain a constant pressure or a constant volume at the surgical site. In other embodiments, the tray may provide an independent set of user controls for the infusion rate, whereby the infusion rate may be adjusted independent of the aspiration rate.

In the embodiment of FIG. 5, the tray also wirelessly communicates with the other instruments in the surgical system through the wireless transceiver 515. In this embodiment, the tray may act as a control device and may be used to control the functionality of some or all of the other instruments. For example, for a vitrectomy procedure, possible wirelessly connected devices may include, an illumination device, a foot pedal, and an external monitor. In some instances, the connected devices may be used to control certain aspects of the system. For example, the foot pedal may provide an alternate mechanism to control the cut speed and the aspiration level of the system. In these instances, the foot pedal may wirelessly send adjustment commands to the tray, where the processing unit routes the adjustment commands to the appropriate destination.

In other instances, one or more of the instruments used to perform the surgical procedure are independently controlled and operated, and user controls for each respective instrument may be provided directly on the instrument. For example, the illumination device may be a portable, self-powered, handheld LED illuminating instrument or comparable illuminating device. Similarly to the cutter controls being provided on the handpiece, illumination controls may be provided directly on the illuminating device to control operating parameters, such as light intensity of the provided illumination. In these instances, the wirelessly connected instruments may still transmit useful statistics, current settings, or status information on the surgical procedure to the tray 505. The tray may further include a display, speakers, or other status indicators 517, for communicating the information to a user of the system. In some embodiments, an external monitor may also be wirelessly connected to the tray, and used to store compiled information on the surgical procedure. The various instruments may also communicate wirelessly with the tray, as well as with each other, to optimize operating parameters.

Figure 6:
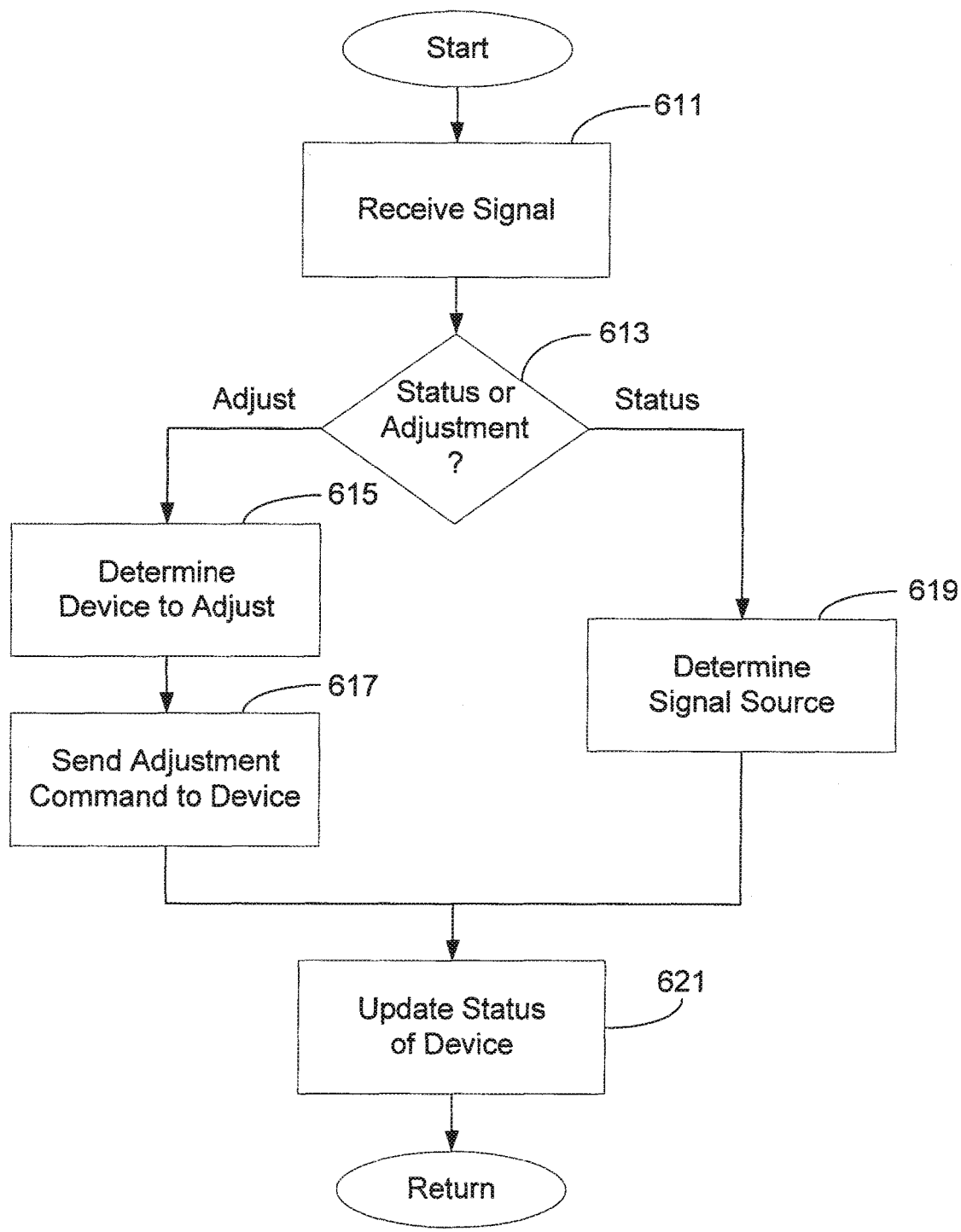
FIG. 6 is a flow diagram of a process executed by the processing unit of the independent surgical center in accordance with one embodiment of the invention.

FIG. 6 is a flow diagram of a process executed by the processing unit 509, 301 of the independent surgical center in accordance with one embodiment of the invention. In some embodiments, the process of FIG. 6 represents the process which is performed by the processing unit housed in the tray in FIG. 5. In some embodiments of the invention, the process may be performed in another instrument or component of the system, based on where the processing unit is located in the system. In some embodiments, the system may include multiple processing units, and the process of FIG. 6 may be performed by one or more of the multiple processing units.

In block 611, the process receives a signal from an instrument in communication with the independent surgical center. In the embodiment illustrated in FIG. 5, the tray 505 may receive the signals from an instrument through a wired connection, for example, the handpiece 503 as illustrated in FIG. 5, or may receive the signals from an instrument through a wireless connection, for example, from the illumination device.

In block 613, the process determines whether the received signal is a status update signal or an adjustment request signal. In some embodiments, the processing unit 509, 301 may be used to adjust operation parameters of selected instruments, and may also be used to process and communicate to a user the status of the same or other instruments. If the processing unit determines that the signal is an adjustment request signal, the process proceeds to block 615. If the processing unit determines that the signal is a status update signal, the process instead proceeds to block 619.

In block 615, the process determines the device for which the adjustment signal is directed. In some embodiments, the adjustment signal may be received by a user control directly connected to the processing unit. For example, in the embodiment of FIG. 5, the adjustment signal may originate from a user control controlling the infusion device located alongside the processing unit in the tray. In other embodiments, the adjustment signal may be received wirelessly from a user control located on a remote instrument, for example, a foot pedal associated with the tray. Some of the adjustment requests may be meant for the device or component from which the signal originated, while some other of the adjustment requests may be meant for a different device, whether it be a device on the tray or on a completely separate instrument in the surgical system. Regardless of the source of the adjustment signal, the processing unit determines the intended destination device or instrument.

In block 617, the process sends an adjustment command to the destination device or instrument. Depending on the configuration of the system, the adjustment command may be an unaltered adjustment signal, where the processing unit acts as a switch or routing device for the system, or the adjustment command may be a wholly new command signal generated by the processing unit based on a received adjustment request signal, for example, a received signal as was described above with respect to block 611. In most embodiments of the system, after an adjustment command is sent to a respective device or instrument, the operational settings or parameters of the device are adjusted in accordance with the adjustment command.

If the signal is a status update signal, the process, in block 619, determines the source of the status update signal. In most embodiments, status update signals include status update information of the device from which the status update signal originated. The status update information may include various information about an originating device, for example, current settings, operating parameters, remaining power levels, instrument fault conditions, and other information. Status information for each specific instrument in the system is different depending on the functionality of the instrument. For example, a handpiece may provide status of cut speed of a cutter or aspiration levels, whereas an illumination device may provide illumination level status.

In block 621, the process updates the status of a device or instrument. Whether the originally received signal was an adjustment signal or a status update signal, the processing unit of the system may update status information pertaining to the received signal. In cases where the signal was an adjustment signal, the processing unit may update the status information of the destination device to which the adjustment request was sent. In cases where the signal was a status update signal, the processor may directly update the status information of the device from which the status update signal originated, based on the contents of the status update signal. The processing unit may display the status updates on, for example, a monitor located on the instrument housing the processing unit. Alternatively, the status updates may be expressed visually through changes to, for example, LED indicators, or aurally through, for example, audio alerts outputted through available speakers. In some embodiments, visual or aural status indicators may be available on various other instruments of the system in addition to, or in lieu of, the instrument housing the processing unit. In these embodiments, the processing unit may send the status update information to an appropriate instrument for output or user feedback purposes. According to one embodiment of the invention, the update information is transmitted to the personal surgical center for logging in a log file generated for the surgical procedure. After the status updates have been applied to or recorded by the system, the process returns.

Figure 7:
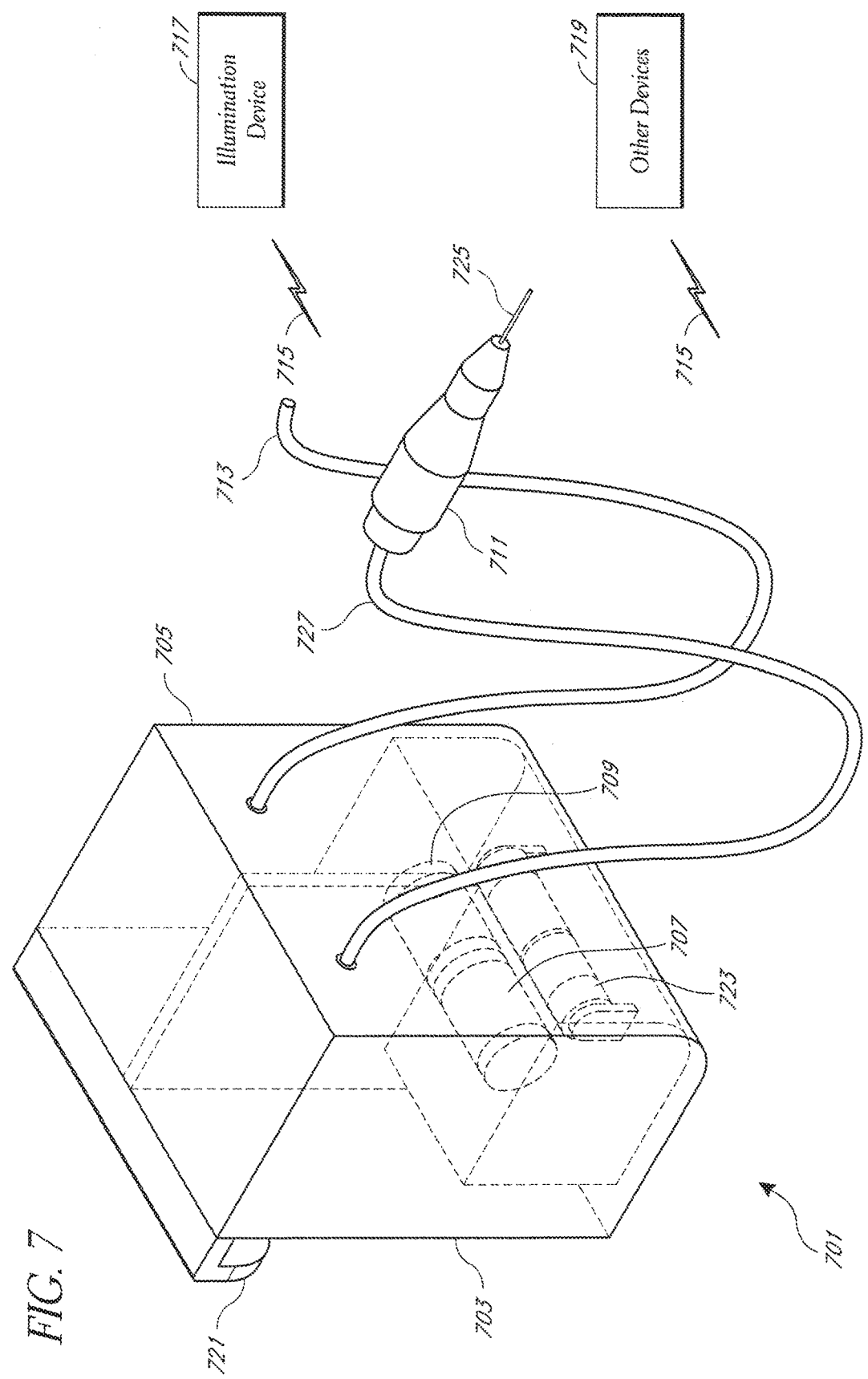
FIG. 7 is an alternate embodiment of an independent surgical center in accordance with aspects of the invention.

FIG. 7 is an alternate embodiment of an independent surgical center in accordance with aspects of the invention. The center illustrated in FIG. 7 is operable independently of an external console, and functions similarly to the system described with respect to FIG. 2b. However, the system of FIG. 7 does not include a tray which acts as a central control unit. Instead, in FIG. 7, the system includes a stand-alone aspiration/infusion cartridge 701, including isolated aspiration 703 and infusion chambers 705, and a separate device for each chamber, for example, an aspiration pump or similar device 707 and an infusion pump or similar device 709. The cartridge is connected to a handpiece 711 and an infusion line 713.

According to the illustrated embodiment, the cartridge 701 as a central control unit instead of the tray as in FIG. 2b. The cartridge is in communication with other surgical instrumentations of the surgical system. The communication is generally established through wireless connections. In this regard, the cartridge is in wireless communication 715 with an illumination device 717 and other devices 719, for example, a foot pedal, an external console, and/or various status indicators associated with the system. In some embodiments, the handpiece and the infusion line may also be integrated in a device separate from the cartridge 701, and be in communication with the cartridge via a wireless connection. In these embodiments, the cartridge may serve as a wireless communication medium between the devices, including the handpiece and the infusion line. In embodiments where the cartridge communicates with an external console, the cartridge generally remains independently operable, with the monitor typically serving as a data collection and storage device. In some embodiments, the external monitor may be capable of serving the system in a larger capacity, for example, by controlling select instruments of the system. However, in most of these embodiments, the system remains independently functional without the external console.

In the embodiment illustrated in FIG. 7, the cartridge is designed to be a free-standing instrument. In some embodiments, the cartridge includes a ledge 721 on the back that allows the cartridge to be hung off other equipment inside the sterile field, for example, a surgical tray or Mayo tray. In some embodiments, the cartridge includes various components and devices for controlling the system, for example, a processing unit, user controls, a power source 723, and a plurality of different interfacing devices which may be similar to the processing unit 301,509, user controls 311, 521, and power source 315, 511 of FIG. 3 or 5. The interfacing devices may include, for example, the aspiration chamber and port for a handpiece, the infusion chamber and port for an infusion line, and a wireless communication interface to communicate with the other instruments of the system. The power source provides power to the cartridge and allows the cartridge to function and be powered independently of other devices, and in some embodiments, provide power to connected devices, such as the handpiece. In some embodiments, the cartridge may also include a display and/or speaker, which may output various status indicators or settings of connected instruments.

In some embodiments, the independent surgical center 10 and individual instruments in the surgical system, including the cartridge, are prepackaged together in sterile packaging. In these embodiments, the packaging may be opened, and the independent surgical center 10 and the individual instruments activated, within the sterile operating field, giving a medical practitioner full access to the instruments and user controls of the independent surgical center 10 within the sterile field. In some embodiments, upon activation, the cartridge may perform an initial scan to determine the available devices or instruments with which it may establish wireless communication for the surgical procedure.

According to one embodiment of the invention, handpiece 711 coupled to the cartridge 701 includes a biological tissue cutter 725, and may be connected to the cartridge via a fluid aspiration line 727. The aspiration line ends in a tip of the handpiece, with the cutter located approximate the tip. User controls located on the cartridge, the handpiece, and/or the infusion line may be available to adjust the aspiration and infusion levels of the system. Operating parameters for other instruments, for example, illumination level, may be controlled directly through the individual devices used to perform each respective function, or may alternatively be controlled at the cartridge if user controls for the other instruments are provided to users on the cartridge.

The cartridge may also act as a feedback or user output system. The cartridge may communicate with the various instruments to retrieve status information and relay the information to a user of the system. In some embodiments, information may be displayed on a built-in display mounted on the cartridge. In other embodiments, other output or user feedback means may be incorporated, for example, LED indicators representing current parameter or status information of the various instruments, or audio alerts when, for example, fault levels are triggered.

Figure 8:
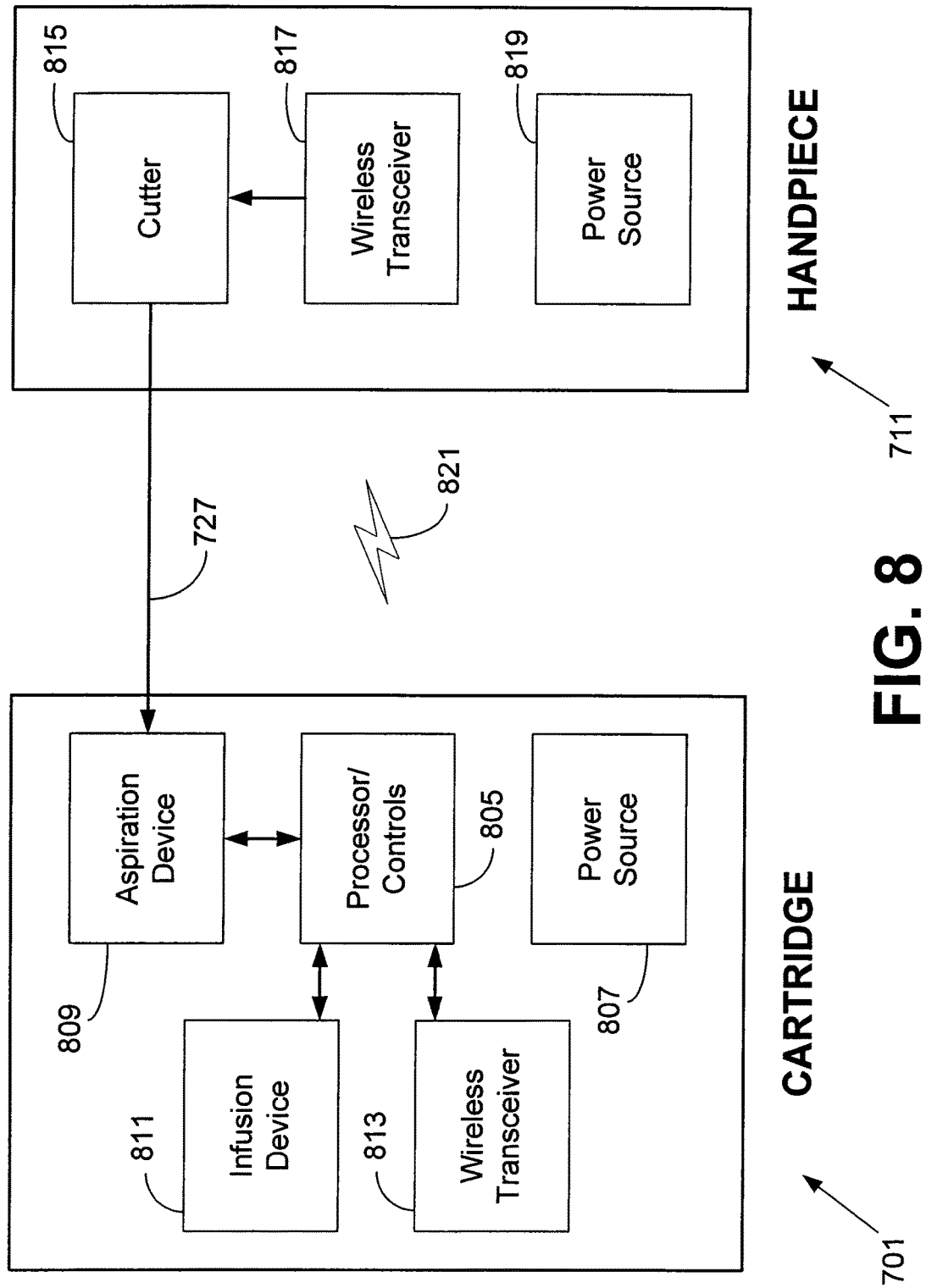
FIG. 8 is a block diagram of an independent surgical center embodied as the infusion/aspiration cartridge in accordance with one embodiment of the invention.

FIG. 8 is a block diagram of an independent surgical center embodied as the infusion/aspiration cartridge 701 of FIG. 7 in accordance with one embodiment of the invention. In many respects, the structure and functionality of the independent surgical center of FIG. 8 are similar to the structure and functionality of the center as discussed in FIG. 5, with a stand-alone aspiration/infusion cartridge substituted into the center in place of the tray. The center includes the handpiece 711 coupled to the cartridge 701. In the embodiment of FIG. 8, the cartridge includes a processing unit and user controls 805, a power source 807, an aspiration device 809, an infusion device 811, and a wireless transceiver 813, while the handpiece includes a biological tissue cutter 815, as well as its own wireless transceiver 817 and its own power source 819.

Having different combinations of components housed in each instrument allows for operational variations between different embodiments. In the embodiment of FIG. 8, for example, the power source in the handpiece provides power to the rest of the components in the handpiece, allowing the handpiece to power up independently of the cartridge. A dedicated power source therefore obviates the need for a power line running between the cartridge and the handpiece. Furthermore, the wireless transceiver housed in the handpiece allows for the handpiece to wirelessly communicate 821 with the cartridge, further obviating the need for an electrical wire or communication line, such as the electrical line described with respect to FIG. 5. Therefore, in the embodiment of FIG. 8, the only remaining connection between the handpiece and the cartridge is the aspiration line 727, which transfers aspirated materials from the handpiece back to an aspiration chamber in the cartridge. In some embodiments, the handpiece may be completely independently operable from the cartridge, if an additional aspiration pump and chamber are, for example, located directly on, or closely attached to, the handpiece. Likewise, with other instruments of the system, each independently operable instrument includes a dedicated power source, and may also include some wireless communication medium if communication with the processor 805 acting as the main source of control is desired.

In the embodiment of FIG. 8, the cartridge does not include a monitor or other status indicators. In some embodiments, there may not be any status indicators provided by the independent surgical center to communicate status information and other useful system information to a user. In other embodiments, different types of status indicators may be located on one or more instruments remote from the independent surgical center. In some of these embodiments, the status indicators located on each individual instrument may correspond to, or be otherwise related to, the function the instrument serves in the context of the surgical system.

Figure 9:
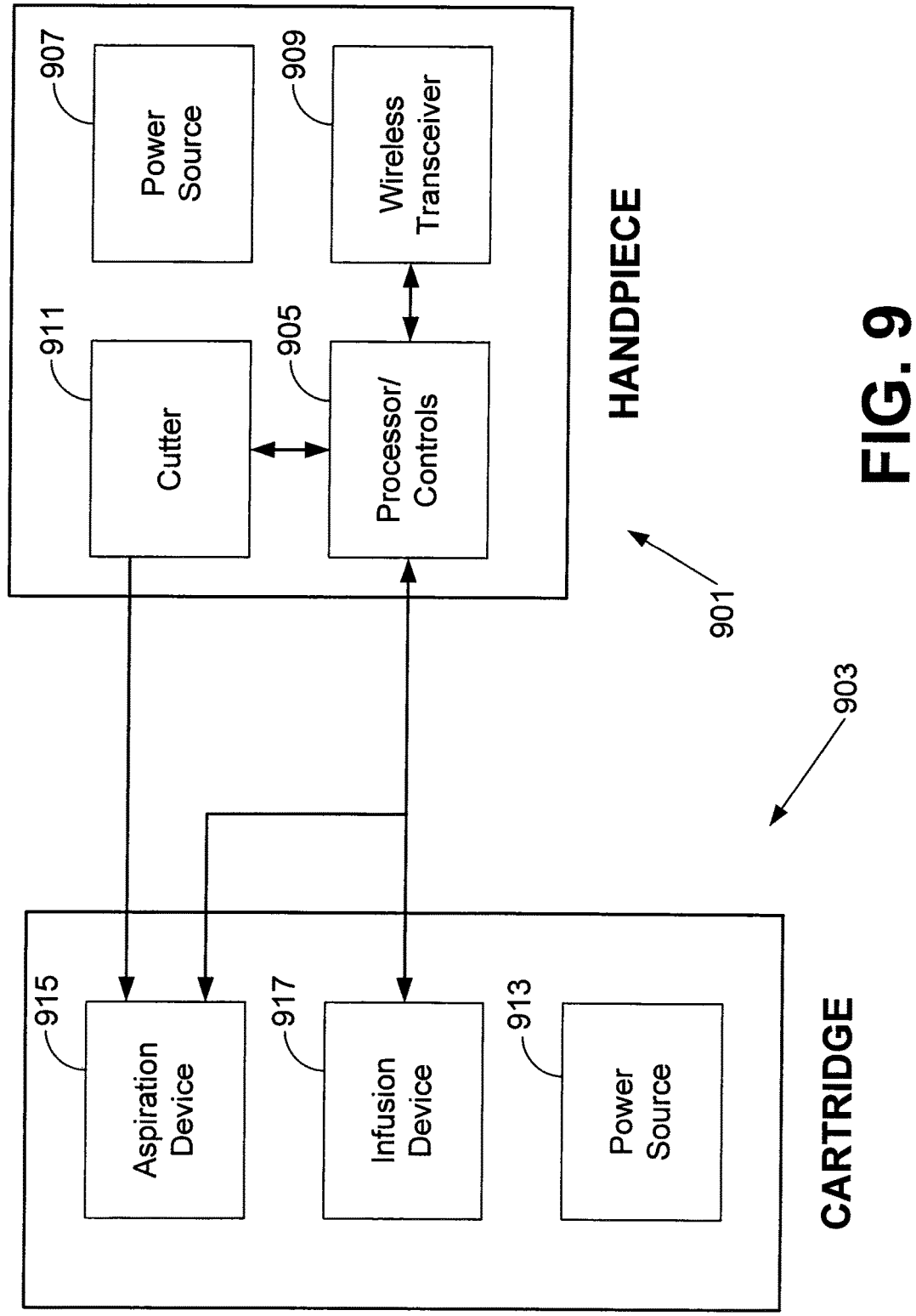
FIG. 9 is a block diagram of yet another alternate embodiment of an independent surgical center in accordance with one embodiment of the invention.

FIG. 9 is a block diagram of yet another alternate embodiment of an independent surgical center in accordance with one embodiment of the invention. FIG. 9 may represent a possible alternate component arrangement for the center of FIG. 7. As has been observed and as was similarly described in FIG. 8, the embodiment illustrated FIG. 9 includes a handpiece 901 interconnected with a cartridge 903. However, in the embodiment illustrated in FIG. 9, the handpiece serves as a processing center of the system instead of the cartridge.

In the embodiment illustrated in FIG. 9, the handpiece includes a processing unit and user controls 905, a power source 907, a wireless transceiver 909, and a biological tissue cutter 911. The cartridge includes a power source 913, an aspiration device 915, and an infusion device 917. The processing unit of the handpiece may serve as the processing center of the system, and establish communication with the various instruments of the system, much like the processing units as described with respect to the tray of FIG. 5 and the cartridge of FIG. 8. Alternatively, in some embodiments, a remote instrument of the system, for example, an illumination device, may instead house the main processing unit of the system. In the embodiment of FIG. 9, a wireless transceiver located in the handpiece is provided for the processing unit to wirelessly communicate with remote instruments of the system. A power source is further provided to power the handpiece. In some embodiments, the wireless transceiver and power source may alternatively be housed in the cartridge, to reduce the size of the handpiece and make it easier for users to handle.

In the embodiment of FIG. 9, the cartridge acts as a supporting instrument to the handpiece. The user controls for the aspiration device and infusion device are located with the processing unit on the handpiece, but may alternatively be located on the cartridge. In embodiments where the user controls are located on the handpiece, adjustment requests may be processed by the processing unit on the handpiece, and adjustment commands generated by the processing unit may be sent to the appropriate device on the cartridge. The processing unit of the handpiece may also control operating parameters of some remote devices with which the handpiece is wirelessly connected. In many embodiments, the processing unit of the handpiece also serves as a status updater, where status update signals are received by the processing unit from various system devices, processed by the processing unit, and communicated to the user of the system, through any of the various feedback or output means as have been previously described.

Other embodiments of the invention may include various different component combinations and functionality differences. For example, the handpiece may include flow sensors for monitoring aspiration levels at the surgical site, or aspiration sensors or detectors may instead be located at or near the aspiration chamber. Further, in some embodiments, an aspiration adjuster or similar device may be located at the handpiece as well, for example, a pinch valve or similar variable orifice. The aspiration level may be monitored and adjusted by controlling the pinch valve or orifice diameter. In these embodiments, pressure at the aspiration chamber may be maintained at a constant level. Various other features may also be incorporated into different instruments of the system. For example, the tray or cartridge may include a port for emptying the aspiration chamber and/or a port for filling or refilling infusion fluid or gas into the infusion chamber. Many other possible features may be incorporated into the individual instrumentation in each respective system.

The different instruments in the independent surgical system as have been described are easily portable, require low capital investment, are efficiently set up and torn down, enable the presence of fewer personnel in the operating room, are adaptable for use in existing surgery centers, and are easily upgradeable. Each instrument is easily moveable into operating rooms, surgery centers, and offices. A doctor's office is a new potential location where various different procedures may be performed. In a doctor's office, space is limited, and using large surgical instrumentation may not always be a realistic option. The highly portable instruments of the invention make setting up for various procedures faster and more convenient, and may allow for certain procedures to be performed even in a doctor's office. Portable surgical systems may also be used by visiting surgeons, and may potentially be taken to and used in remote locations, such as, for example, economically disadvantaged nations. Along those same lines, the instruments described are also low in cost. The instruments used in the systems discussed above are generally all manufactured as disposable units designed for a single use.

In addition, setup times for the system are vastly reduced. In most embodiments of the invention, system initialization and communication establishment between the different instruments is automatic, and most instruments are configured to be immediately ready for use. Connections, for example, an aspiration line running between a handpiece and a tray or cartridge, may be made before packaging, and infusion supplies may be prepackaged for each system. Furthermore, there are generally no additional wires to connect, and no central console to which each individual instrument need be manually connected. Once a procedure has been completed, the instruments may be discarded. In some embodiments, some instruments, for example, aspiration and infusion pumps or devices, may be sent back to a manufacturer for recycling or reuse.

Below are descriptions of other embodiments of a portable biological tissue cutter and infusion/aspiration cassette that may function separate from the independent surgical center.

Biological Tissue Cutting and Aspiration Handpiece

According to one embodiment, the biological tissue cutting and aspiration handpiece (e.g. vitrectomy handpiece or other like handpieces) is portable, lightweight and can be powered by battery to power the cutter and/or aspiration. It can be used in the field, offices, surgery centers and operating rooms. The biological tissue cutting and aspiration handpiece may be used as a standalone instrument or in conjunction with the independent surgical center discussed above. The handpiece may be disposable and is connected to the aspiration/infusion cassette, which provides aspiration pressure to the cutter. FIG. 7 illustrates an exemplary aspiration/infusion cassette 701 with the infusion line 713 appearing on the right and the biological tissue cutting and aspiration handpiece appearing on the left. The left side of the cassette functions to provide aspiration pressure to the biological tissue cutting and aspiration handpiece, while the right side provides infusion.

In one embodiment, for example, the biological tissue cutting and aspiration handpiece is a disposable handpiece such as that described in co-pending U.S. patent application Ser. No. 11/963,749 entitled Disposable Vitrectomy Handpiece, filed Dec. 21, 2007, the entire content of which is incorporated herein by reference. In addition, the biological tissue cutting and aspiration handpiece may incorporate battery power and a flow controller/pinch valve. The handpiece may wirelessly communicate (e.g. Bluetooth) with other surgical instruments, an internal or external monitor or speaker, or a control center in the aspiration/infusion cassette. Alternatively, the handpiece may wirelessly communicate with a personal surgical center, as described for example in U.S. patent application entitled Personal Surgical Center, filed on even date herewith. Surgical parameters (e.g. cut speed, aspiration pressure/flow rate) may be controlled directly on the handpiece, or via a foot pedal wirelessly connected to the handpiece. Such parameters may control a cutting tip, aspiration pump, and the like. The drive circuitry may be incorporated directly in the handpiece, in the surgical tray, or aspiration/infusion cassette depending on how the handpiece is powered (i.e. by battery or through the aspiration/infusion cassette).

As noted above, according to one embodiment, the biological tissue cutting and aspiration handpiece is a standalone instrument, not used with an external control center. In this embodiment, the handpiece is used in conjunction with other standalone instrumentation, such as an illumination device. The controls for the handpiece are located on the handpiece itself, eliminating the need for a surgical console. The handpiece itself or the surgical tray may have a display or speaker to inform the surgeon of current surgical settings and instrument faults. According to one embodiment, the handpiece includes a control unit which may be, for example, a microprocessor based unit, an ASIC, or the like, and other circuitry described with respect to FIG. 9.

In another embodiment, as also noted above, the biological tissue cutting and aspiration handpiece can be used in conjunction with an aspiration/infusion cassette that includes a control center or in conjunction with an external, laptop control center. Although it may be possible to plug the system into an outlet, battery power enables better maneuverability of the handpiece. The battery may be placed inside the handpiece, surgical tray or at the aspiration/infusion cassette itself. When the battery is placed inside the handpiece, it adds weight and size to the unit, reducing maneuverability and ergonomics. The aspiration/infusion cassette can be larger and heavier because ergonomics on this instrument are not as critical. However, when the battery is placed at the aspiration/infusion cassette or surgical tray, an electrical line would need to be tethered to the handpiece along with the aspiration line.

The wireless control (e.g. Bluetooth) may be mounted in the handpiece, the aspiration/infusion cassette, the surgical tray or all of the above. This will depend on how the device is configured. If the handpiece uses battery power and includes no link to the aspiration cassette or surgical tray, wireless communication will need to be mounted on all units. However, if there is a direct-wired link between the two, wireless communications may then be mounted on either unit. In one embodiment, the wireless communication will be mounted on the aspiration/infusion cassette or surgical tray to reduce the weight of the handpiece. FIG. 5 illustrates a system in which the battery power for the biological tissue cutting and aspiration handpiece, the wireless communication and the aspiration all originate from the surgical tray.

As noted above, the handpiece may include a display or speaker for relaying information regarding instrument status, fault, cut speed etc. For example, the handpiece may include a LED or speaker on the handpiece itself. Alternatively, the instrument and operation information may be indicated on a display or speaker on the surgical tray or may be displayed on a laptop center.

When used in conjunction with a laptop center, the biological tissue cutting and aspiration handpiece may communicate with the laptop directly or indirectly through the surgical tray. The laptop center can indicate the instrument and operation information, such as current cut speed, battery life (if applicable), and any faults. It may also receive additional information, such as the maximum cut speed permissible and other surgical parameters. Upon startup, the biological tissue cutting and aspiration handpiece can identify itself to the laptop center and indicate whether it has been used before.

If flow sensing or flow control is used, the sensors and actuators may be placed close to or directly on the biological tissue cutting and aspiration handpiece. Aspiration/Infusion Cassette.

According to one embodiment, the aspiration/infusion cassette is portable, lightweight, and attached to a biological tissue cutting and aspiration handpiece and infusion line. According to one embodiment, the aspiration/infusion cassette is made integral with the surgical tray, but according to one embodiment, the cassette is separate from the tray. In this latter embodiment, the cassette includes a control unit which may be, for example, a microprocessor based unit, an ASIC, or the like, and other circuitry described with respect to FIG. 8 which allows the cassette be the center of control with respect to the cassette and/or the biological tissue cutting device.

The cassette may be used in the field, offices, surgery centers and operating rooms. The cassette may be used as a stand-alone instrument or in conjunction with a surgical center, such as the one discussed above. Alternatively, the cassette may be used in conjunction with a personal surgical center, such as that described in co-pending U.S. patent application entitled Personal Surgical Center filed on even date herewith.

The aspiration/infusion cassette includes infusion fluid (such as BSS) and an aspiration line. Aspiration is applied to a portable surgical handpiece, such as the biological tissue cutting and aspiration handpiece described above. Infusion is attached to an infusion line. In one embodiment, the aspiration/infusion cassette includes a cassette for gas-fluid exchange system. Additionally, there may be ports to allow filling the BSS container (if required) or emptying the aspiration cassette. Furthermore, from the filling port, a surgeon may put in glucose or other medication (e.g. dyes for visualization) for certain cases into the infusion cassette.

When the aspiration/infusion cassette is used in conjunction with a personal surgical center, it is powered separately from the center. Although it may be possible to plug the system into an outlet power, battery power enables better maneuverability. The battery can be placed in the cassette itself or in the surgical tray, and powers any vacuum or infusion pumps as well as the biological tissue cutting and aspiration handpiece. Power to the cassette can be turned on once the cassette or surgical tray is removed from the packaging (e.g. by turning on a switch, button, etc.). This will initiate communication with the personal surgical center, if present.

In one embodiment, the aspiration/infusion cassette is a free-standing instrument. The vacuum source may be directly mounted on the cassette itself. It may be a vacuum based system, similar to the venturi system, or a flow based system (peristaltic pump). Any suitable vacuum based system may be used, for example, the vacuum source may consist of a small, battery powered vacuum pump providing vacuum pressure to the handpiece. Alternatively, the vacuum source may be a motor controlling a syringe/piston or pump to apply vacuum pressure. The vacuum source may provide a constant vacuum level, charging only when required, or it may allow for variable vacuum settings. For flow based vacuum, a small electric pump is added to the cassette instead of the peristaltic pump.

The aspiration/infusion cassette communicates with the personal surgical center (when present) via a wireless link. When no center is used, the cassette may communicate wirelessly with other instrumentation, such as the biological tissue cutter or illumination handpiece.

The cassette may also include a pre-packaged vacuum source, which would be shipped as an evacuated container. To use, the seal is broken, and the vacuum is applied to the handpiece. However, if vacuum is lost, the cassette cannot be re-charged.

Flow control for aspiration can be controlled from the surgical handpiece. The flow control may be on the handle or on a foot pedal which may be wirelessly connected. Infusion control may be on the surgical handpiece, on a foot pedal, controlled by an IV pole height, or by a switch on the aspiration/infusion cassette itself.

Vacuum at the cassette may be constant or variable. With variable vacuum level control, the level of vacuum is modified based on surgical settings. Vacuum is directly attached to the vitrectomy aspiration line, and flow is based on vacuum level.

If vacuum is maintained constant at the cassette, a pinch valve/variable orifice may be used to modulate flow. In this scenario, full vacuum would be maintained in the cassette and applied for substantially all of the time to the back of the aspiration line. The pinch valve would be used to modulate the flow level. A pressure sensor could be mounted upstream (closest to the biological tissue cutting and aspiration handpiece) from the pinch valve. This would monitor the actual pressure and permit accurate pinch valve settings in a continuous manner. A flow sensor may be used to measure flow rate instead of the pressure sensor. Flow can be modulated by adjusting the pinch valve. In either scenario, surging would be reduced by monitoring flow close to the handpiece. For a flow based system, the surgeon would control the rate at which the vacuum pump removes tissue from the eye. Flow may be monitored by a sensor at the cassette or at the surgical instrument handpiece. This could be used for feedback on the flow conditions.

Infusion can be applied from a small disposable pump, a Harvard type apparatus mechanism, a spring loaded syringe, small fluid pump, or by mounting the unit on an IV pole. A pre-packaged amount of sterile balanced salt solution (BSS) is provided for the procedure. The volume of BSS is the same as or smaller than the volume of the aspiration cassette.

If a disposable pump is used in the cassette, it may pressurize the cassette causing the BSS to enter the eye. A filter may be required to keep the inside of the infusion cassette free of airborne particles. Alternatively, a small sealed infusion bag may be mounted to the infusion line. The chamber around the infusion line is pressurized, causing the infusion fluid to enter the eye and not come in direct contact with the pressurized air. A peristaltic pump may also be used to infuse the eye. Alternatively, a Harvard type apparatus or spring compressed syringe may be used to infuse the BSS.

If an IV pole is used, the cassette could hang from many different IV pole designs. Furthermore, a specific IV pole may be designed to work with the cassette. In this scenario, there would be a place for the cassette to fit and the IV pole may provide power for the aspiration pump. No infusion pump would be required for maintaining eye pressure.

As noted above, the aspiration/infusion module may communicate with a personal surgical center if such a center is used. It will send status information regarding the state of the instruments, and receive information that may change operable parameters. Once the aspiration/infusion cassette is turned on, it will communicate with the personal surgical center to indicate serial number, if it has been used before, and the type of instrumentation being used (25 versus 23-gauge instrumentation), which vitrectomy probe is being used, etc. The cassette can also communicate the status of the battery and any instrument faults that may occur.

A wireless control may be mounted on the biological tissue cutting and aspiration handpiece, the aspiration/infusion cassette, illuminator, surgical tray, or all of the above. This will depend on how the device is configured. If the biological tissue cutting and aspiration handpiece uses battery power and is not directly linked to the aspiration cassette, wireless communication is mounted on both units. If there is a direct wired link between the two, wirelesses communication may be mounted on either unit, but need not be mounted on both units. In one embodiment, the wireless communication is mounted on the cassette to reduce the weight of the handpiece.

The aspiration/infusion cassette may include a chamber for gas-fluid exchange in the eye. This could be a syringe filled with the appropriate gas or mixture of gases. A Harvard type apparatus, spring mechanism, or pump could also be used to administer gas-fluid exchange. The gas line would be connected to the infusion line. A remote switch could be used to commence gas exchange. The button for this may be on the illumination device, surgical tray, the biological tissue cutting and aspiration handpiece, or any other suitable location. The specific gases used depend on the specific procedures performed.

Instrument settings, operational parameters, and status may be displayed on the aspiration/infusion cassette itself. Alternatively, this information can be directed to and displayed on the independent surgical center, the cassette, or on the personal surgical center connected (either directly or wirelessly) to the cassette. In another embodiment, the information is displayed on an external monitor or through a speaker connected (either directly or wirelessly) to the cassette. The information displayed may include bottle infusion pressure, cut speed for the vitrectomy probe, fault conditions, conditions of batteries, and other operational parameters.

The cassette may include a ledge on the back of the cassette that allows the cassette to be hung off the surgical tray. Alternatively, the cassette is incorporated into the tray. The aspiration and infusion pump(s) and battery may be separate from the aspiration/infusion cassettes, allowing the surgeon to break off the aspiration and infusion cassettes after the procedure and dispose of them. The pump or battery component may be refurbishment and then re-deployed.

Although the invention has been described with respect to certain specific embodiments, those skilled in the art will have no difficulty devising variations to the described embodiments which in no way depart from the scope and spirit of the present invention. Furthermore, to those skilled in the various arts, the invention herein may suggest solutions to other tasks and adaptations for other applications. It is the Applicants' intention to cover all such uses of the invention, and those changes and modifications which could be made to the embodiments of the invention herein chosen for the purpose of disclosure without departing from the spirit and scope of the invention. Thus, the present embodiments of the invention should be considered in all respects as illustrative and not restrictive.

What is claimed:

1. A self-powered surgical system for a surgical procedure, comprising:
    a surgical tray;
    a plurality of handheld instruments;
    a power source in at least one of the surgical tray and a handheld instrument;
    and a processing unit;
    wherein the processing unit is configured to execute program instructions, the program instructions including instructions for:
        detecting power from the at least one power source;
        directing power to the plurality of handheld instruments from the at least one power source;
        wirelessly detect identification information from at least one of the plurality of handheld instruments;
        establishing communication with each of the plurality of handheld instruments; and
        transmit an initial configuration setting to at least one of the plurality of handheld instruments based on the identification information.

2. The system of claim 1, wherein the program instructions further include instructions for:
    receiving an adjustment request for a one of the plurality of handheld instruments; and
    adjusting operating parameters of the one of the plurality of handheld instruments based on the adjustment request.

3. The system of claim 2, wherein each adjustment request is received from a one of the plurality of handheld instruments.

4. The system of claim 1, wherein the processing unit is housed in the surgical tray.

5. The system of claim 4, wherein the plurality of handheld instruments and the at least one power source are packaged with the surgical tray prior to the surgical procedure.

6. The system of claim 5, wherein the package is sterile.

7. The system of claim 6, wherein each of the plurality of handheld instruments is useable within a sterile barrier during the surgical procedure.

8. The system of claim 6, wherein the plurality of handheld instruments are configured to be used within a substantially sterile barrier during the surgical procedure and are further configured to be accessed by a substantially non-sterile assistant.

9. The system of claim 1, wherein at least one of the plurality of handheld instruments is physically connected to the surgical tray.

10. The system of claim 1, wherein the program instructions further include instructions for:
    receiving a status update signal from a one of the plurality of handheld instruments; and
    adjusting a status indicator associated with the one of the plurality of handheld instruments based on the status update signal.

11. The system of claim 1, wherein the processing unit is housed in one of the plurality of handheld instruments.

12. The system of claim 1, wherein each of the plurality of handheld instruments includes a radio frequency identification tag to facilitate establishment of communication with the processing unit.

13. A portable biological cutting and aspiration device comprising:
    a cutting tip;
    a fluid aspiration device; and
    an integrated control unit coupled to the fluid aspiration device and wirelessly coupled to the cutting tip, wherein the control unit is configured to control cutting and aspiration of the cutting tip and fluid aspiration device.

14. A portable infusion and aspiration device comprising:
    an aspiration chamber;
    an aspiration line coupled to a biological tissue cutting and aspiration device, the aspiration line configured to suction matter dislodged from a surgical site into the aspiration chamber;
    a wireless transceiver wirelessly coupled to a biological tissue cutting and aspiration device, the wireless transceiver configured to wirelessly communicate with the biological tissue cutting and aspiration device;
    an infusion chamber having an infusion solution; and
    an infusion line coupled to the infusion chamber and configured to inject the infusion solution to the surgical site for maintaining pressure in the surgical site,
    wherein the aspiration chamber and infusion chamber are included in a single, disposable cassette.

* * * * *